(12) United States Patent
Mazlish et al.

(10) Patent No.: US 11,969,579 B2
(45) Date of Patent: *Apr. 30, 2024

(54) INSULIN DELIVERY METHODS, SYSTEMS AND DEVICES

(71) Applicant: Insulet Corporation, Acton, MA (US)

(72) Inventors: Bryan Mazlish, Palo Alto, CA (US); Lane Desborough, Thousand Oaks, CA (US)

(73) Assignee: Insulet Corporation, Acton, MA (US)

( * ) Notice: Subject to any disclaimer, the term of this patent is extended or adjusted under 35 U.S.C. 154(b) by 191 days.

This patent is subject to a terminal disclaimer.

(21) Appl. No.: 17/303,974

(22) Filed: Jun. 11, 2021

(65) Prior Publication Data

US 2021/0299354 A1   Sep. 30, 2021

Related U.S. Application Data

(63) Continuation of application No. 15/870,717, filed on Jan. 12, 2018, now Pat. No. 11,033,682.

(Continued)

(51) Int. Cl.
*A61M 5/172* (2006.01)
*A61B 5/145* (2006.01)
(Continued)

(52) U.S. Cl.
CPC ....... *A61M 5/1723* (2013.01); *A61B 5/14532* (2013.01); *A61M 5/14248* (2013.01);
(Continued)

(58) Field of Classification Search
None
See application file for complete search history.

(56) References Cited

U.S. PATENT DOCUMENTS

| 303,013 A | 8/1884 | Hortoxr |
| 445,545 A | 2/1891 | Crane |

(Continued)

FOREIGN PATENT DOCUMENTS

| AU | 2015200829 A1 | 3/2015 |
| AU | 2015200834 A1 | 3/2015 |

(Continued)

OTHER PUBLICATIONS

US 5,954,699 A, 09/1999, Jost et al. (withdrawn)

(Continued)

*Primary Examiner* — Manuel A Mendez
(74) *Attorney, Agent, or Firm* — TraskBritt

(57) ABSTRACT

A method of insulin delivery, the method may include obtaining one or more blood glucose readings of a user, and, based on the blood glucose readings, generating a set of insulin delivery actions that may include delivery of a baseline basal rate or predefined variations of the baseline basal rate. The method may also include monitoring previous insulin delivery actions to the user to determine whether the previous insulin delivery actions include insulin beyond a threshold amount, where the previous insulin delivery actions may include delivery of the baseline basal rate or predefined variations of the baseline basal rate, and, based on the previous insulin delivery actions including insulin beyond the threshold amount, adjusting the set of insulin delivery actions.

20 Claims, 7 Drawing Sheets

Related U.S. Application Data

(60) Provisional application No. 62/563,836, filed on Sep. 27, 2017, provisional application No. 62/563,804, filed on Sep. 27, 2017, provisional application No. 62/446,236, filed on Jan. 13, 2017.

(51) Int. Cl.
  *A61M 5/142* (2006.01)
  *G16H 20/17* (2018.01)
  *A61B 5/00* (2006.01)
  *A61K 38/28* (2006.01)
  *A61M 5/00* (2006.01)
  *A61M 5/315* (2006.01)

(52) U.S. Cl.
  CPC ............ *G16H 20/17* (2018.01); *A61B 5/4839* (2013.01); *A61K 38/28* (2013.01); *A61M 5/003* (2013.01); *A61M 5/31568* (2013.01); *A61M 2205/35* (2013.01); *A61M 2205/502* (2013.01); *A61M 2205/52* (2013.01); *A61M 2230/201* (2013.01)

(56) References Cited

U.S. PATENT DOCUMENTS

| | | |
|---|---|---|
| 588,583 A | 8/1897 | Lade |
| 1,441,508 A | 1/1923 | Marius et al. |
| 2,283,925 A | 5/1942 | Harvey |
| 2,797,149 A | 6/1957 | Skeggs |
| 2,886,529 A | 5/1959 | Guillaud |
| 3,413,573 A | 11/1968 | Nathanson et al. |
| 3,574,114 A | 4/1971 | Monforte |
| 3,614,554 A | 10/1971 | Shield et al. |
| 3,631,847 A | 1/1972 | Hobbs |
| 3,634,039 A | 1/1972 | Brondy |
| 3,812,843 A | 5/1974 | Wootten et al. |
| 3,841,328 A | 10/1974 | Jensen |
| 3,885,662 A | 5/1975 | Schaefer |
| 3,963,380 A | 6/1976 | Thomas et al. |
| 3,983,077 A | 9/1976 | Fuller et al. |
| 4,055,175 A | 10/1977 | Clemens et al. |
| 4,108,177 A | 8/1978 | Pistor |
| 4,146,029 A | 3/1979 | Ellinwood, Jr. |
| 4,151,845 A | 5/1979 | Clemens |
| 4,245,634 A | 1/1981 | Albisser et al. |
| 4,268,150 A | 5/1981 | Chen |
| 4,295,176 A | 10/1981 | Wittwer |
| 4,313,439 A | 2/1982 | Babb et al. |
| 4,368,980 A | 1/1983 | Aldred et al. |
| 4,373,527 A | 2/1983 | Fischell |
| 4,400,683 A | 8/1983 | Eda et al. |
| 4,403,984 A | 9/1983 | Ash et al. |
| 4,424,720 A | 1/1984 | Bucchianeri |
| 4,435,173 A | 3/1984 | Siposs et al. |
| 4,464,170 A | 8/1984 | Clemens et al. |
| 4,469,481 A | 9/1984 | Kobayashi |
| 4,475,901 A | 10/1984 | Kraegen et al. |
| 4,498,843 A | 2/1985 | Schneider et al. |
| 4,507,115 A | 3/1985 | Kambara et al. |
| 4,523,170 A | 6/1985 | Huth, III |
| 4,526,568 A | 7/1985 | Clemens et al. |
| 4,526,569 A | 7/1985 | Bernardi |
| 4,529,401 A | 7/1985 | Leslie et al. |
| 4,551,134 A | 11/1985 | Slavik et al. |
| 4,559,033 A | 12/1985 | Stephen et al. |
| 4,559,037 A | 12/1985 | Franetzki et al. |
| 4,562,751 A | 1/1986 | Nason et al. |
| 4,573,968 A | 3/1986 | Parker |
| 4,585,439 A | 4/1986 | Michel |
| 4,601,707 A | 7/1986 | Albisser et al. |
| 4,624,661 A | 11/1986 | Arimond |
| 4,633,878 A | 1/1987 | Bombardieri |
| 4,634,427 A | 1/1987 | Hannula et al. |
| 4,646,038 A | 2/1987 | Wanat |
| 4,657,529 A | 4/1987 | Prince et al. |
| 4,678,408 A | 7/1987 | Nason et al. |
| 4,684,368 A | 8/1987 | Kenyon |
| 4,685,903 A | 8/1987 | Cable et al. |
| 4,731,726 A | 3/1988 | Allen, III |
| 4,743,243 A | 5/1988 | Vaillancourt |
| 4,755,169 A | 7/1988 | Sarnoff et al. |
| 4,755,173 A | 7/1988 | Konopka et al. |
| 4,759,120 A | 7/1988 | Bernstein |
| 4,781,688 A | 11/1988 | Thoma et al. |
| 4,781,693 A | 11/1988 | Martinez et al. |
| 4,808,161 A | 2/1989 | Kamen |
| 4,854,170 A | 8/1989 | Brimhall et al. |
| 4,859,492 A | 8/1989 | Rogers et al. |
| 4,880,770 A | 11/1989 | Mir et al. |
| 4,886,499 A | 12/1989 | Cirelli et al. |
| 4,898,578 A | 2/1990 | Rubalcaba, Jr. |
| 4,898,579 A | 2/1990 | Groshong et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,944,659 A | 7/1990 | Labbe et al. |
| 4,967,201 A | 10/1990 | Rich, III |
| 4,969,874 A | 11/1990 | Michel et al. |
| 4,975,581 A | 12/1990 | Robinson et al. |
| 4,976,720 A | 12/1990 | MacHold et al. |
| 4,981,140 A | 1/1991 | Wyatt |
| 4,994,047 A | 2/1991 | Walker et al. |
| 5,007,286 A | 4/1991 | Malcolm et al. |
| 5,007,458 A | 4/1991 | Marcus et al. |
| 5,061,424 A | 10/1991 | Karimi et al. |
| 5,062,841 A | 11/1991 | Siegel |
| 5,084,749 A | 1/1992 | Losee et al. |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,130,675 A | 7/1992 | Sugawara |
| 5,134,079 A | 7/1992 | Cusack et al. |
| 5,139,999 A | 8/1992 | Gordon et al. |
| 5,153,827 A | 10/1992 | Coutre et al. |
| 5,154,973 A | 10/1992 | Imagawa et al. |
| 5,165,406 A | 11/1992 | Wong |
| 5,176,662 A | 1/1993 | Bartholomew et al. |
| 5,178,609 A | 1/1993 | Ishikawa |
| 5,189,609 A | 2/1993 | Tivig et al. |
| 5,198,824 A | 3/1993 | Poradish |
| 5,205,819 A | 4/1993 | Ross et al. |
| 5,207,642 A | 5/1993 | Orkin et al. |
| 5,213,483 A | 5/1993 | Flaherty et al. |
| 5,217,754 A | 6/1993 | Santiago-Aviles et al. |
| 5,219,377 A | 6/1993 | Poradish |
| 5,232,439 A | 8/1993 | Campbell et al. |
| 5,237,993 A | 8/1993 | Skrabal |
| 5,244,463 A | 9/1993 | Cordner et al. |
| 5,254,096 A | 10/1993 | Rondelet et al. |
| 5,257,980 A | 11/1993 | Van et al. |
| 5,261,882 A | 11/1993 | Sealfon |
| 5,263,198 A | 11/1993 | Geddes et al. |
| 5,272,485 A | 12/1993 | Mason et al. |
| 5,273,517 A | 12/1993 | Barone et al. |
| 5,281,202 A | 1/1994 | Weber et al. |
| 5,281,808 A | 1/1994 | Kunkel |
| 5,299,571 A | 4/1994 | Mastrototaro |
| 5,308,982 A | 5/1994 | Ivaldi et al. |
| 5,342,298 A | 8/1994 | Michaels et al. |
| 5,346,476 A | 9/1994 | Elson |
| 5,364,342 A | 11/1994 | Beuchat et al. |
| 5,377,674 A | 1/1995 | Kuestner |
| 5,380,665 A | 1/1995 | Cusack et al. |
| 5,385,539 A | 1/1995 | Maynard |
| 5,389,078 A | 2/1995 | Zalesky et al. |
| 5,403,797 A | 4/1995 | Ohtani et al. |
| 5,411,889 A | 5/1995 | Hoots et al. |
| 5,421,812 A | 6/1995 | Langley et al. |
| 5,427,988 A | 6/1995 | Sengupta et al. |
| 5,433,710 A | 7/1995 | Vanantwerp et al. |
| 5,456,945 A | 10/1995 | McMillan et al. |

(56) References Cited

U.S. PATENT DOCUMENTS

| | | |
|---|---|---|
| 5,468,727 A | 11/1995 | Phillips et al. |
| 5,478,610 A | 12/1995 | Desu et al. |
| 5,505,709 A | 4/1996 | Funderburk et al. |
| 5,505,828 A | 4/1996 | Wong et al. |
| 5,507,288 A | 4/1996 | Boecker et al. |
| 5,513,382 A | 4/1996 | Agahi-Kesheh et al. |
| 5,533,389 A | 7/1996 | Kamen et al. |
| 5,535,445 A | 7/1996 | Gunton |
| 5,540,772 A | 7/1996 | McMillan et al. |
| 5,543,773 A | 8/1996 | Evans et al. |
| 5,558,640 A | 9/1996 | Pfeiler et al. |
| 5,569,186 A | 10/1996 | Lord et al. |
| 5,582,593 A | 12/1996 | Hultman |
| 5,584,053 A | 12/1996 | Kommrusch et al. |
| 5,584,813 A | 12/1996 | Livingston et al. |
| 5,590,387 A | 12/1996 | Schmidt et al. |
| 5,609,572 A | 3/1997 | Lang |
| 5,614,252 A | 3/1997 | McMillan et al. |
| 5,625,365 A | 4/1997 | Tom et al. |
| 5,635,433 A | 6/1997 | Sengupta |
| 5,637,095 A | 6/1997 | Nason et al. |
| 5,665,065 A | 9/1997 | Colman et al. |
| 5,665,070 A | 9/1997 | McPhee |
| 5,678,539 A | 10/1997 | Schubert et al. |
| 5,685,844 A | 11/1997 | Marttila |
| 5,685,859 A | 11/1997 | Kornerup |
| 5,693,018 A | 12/1997 | Kriesel et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,707,459 A | 1/1998 | Itoyama et al. |
| 5,707,715 A | 1/1998 | Derochemont et al. |
| 5,713,875 A | 2/1998 | Tanner, II |
| 5,714,123 A | 2/1998 | Sohrab |
| 5,716,343 A | 2/1998 | Kriesel et al. |
| 5,722,397 A | 3/1998 | Eppstein |
| 5,733,259 A | 3/1998 | Valcke et al. |
| 5,741,228 A | 4/1998 | Lambrecht et al. |
| 5,746,217 A | 5/1998 | Erickson et al. |
| 5,747,350 A | 5/1998 | Sattler |
| 5,747,870 A | 5/1998 | Pedder |
| 5,748,827 A | 5/1998 | Holl et al. |
| 5,755,682 A | 5/1998 | Knudson et al. |
| 5,758,643 A | 6/1998 | Wong et al. |
| 5,759,923 A | 6/1998 | McMillan et al. |
| 5,764,189 A | 6/1998 | Lohninger |
| 5,771,567 A | 6/1998 | Pierce et al. |
| 5,776,103 A | 7/1998 | Kriesel et al. |
| 5,779,676 A | 7/1998 | Kriesel et al. |
| 5,785,688 A | 7/1998 | Joshi et al. |
| 5,797,881 A | 8/1998 | Gadot |
| 5,800,397 A | 9/1998 | Wilson et al. |
| 5,800,405 A | 9/1998 | McPhee |
| 5,800,420 A | 9/1998 | Gross et al. |
| 5,801,057 A | 9/1998 | Smart et al. |
| 5,804,048 A | 9/1998 | Wong et al. |
| 5,807,075 A | 9/1998 | Jacobsen et al. |
| 5,817,007 A | 10/1998 | Fodgaard et al. |
| 5,820,622 A | 10/1998 | Gross et al. |
| 5,823,951 A | 10/1998 | Messerschmidt |
| 5,839,467 A | 11/1998 | Saaski et al. |
| 5,840,020 A | 11/1998 | Heinonen et al. |
| D403,313 S | 12/1998 | Peppel |
| 5,848,991 A | 12/1998 | Gross et al. |
| 5,851,197 A | 12/1998 | Marano et al. |
| 5,854,608 A | 12/1998 | Leisten |
| 5,858,005 A | 1/1999 | Kriesel |
| 5,858,239 A | 1/1999 | Kenley et al. |
| 5,859,621 A | 1/1999 | Leisten |
| 5,865,806 A | 2/1999 | Howell |
| 5,871,470 A | 2/1999 | McWha |
| 5,879,310 A | 3/1999 | Sopp et al. |
| 5,889,459 A | 3/1999 | Hattori et al. |
| 5,891,097 A | 4/1999 | Saito et al. |
| 5,892,489 A | 4/1999 | Kanba et al. |
| 5,897,530 A | 4/1999 | Jackson |
| 5,902,253 A | 5/1999 | Pfeiffer et al. |
| 5,903,421 A | 5/1999 | Furutani et al. |
| 5,906,597 A | 5/1999 | McPhee |
| 5,911,716 A | 6/1999 | Rake et al. |
| 5,919,167 A | 7/1999 | Mulhauser et al. |
| 5,931,814 A | 8/1999 | Alex et al. |
| 5,932,175 A | 8/1999 | Knute et al. |
| 5,933,121 A | 8/1999 | Rainhart et al. |
| 5,935,099 A | 8/1999 | Peterson et al. |
| 5,945,963 A | 8/1999 | Leisten |
| 5,947,911 A | 9/1999 | Wong et al. |
| 5,957,890 A | 9/1999 | Mann et al. |
| 5,961,492 A | 10/1999 | Kriesel et al. |
| 5,965,848 A | 10/1999 | Altschul et al. |
| 5,971,941 A | 10/1999 | Simons et al. |
| 5,993,423 A | 11/1999 | Choi |
| 5,997,501 A | 12/1999 | Gross et al. |
| 6,005,151 A | 12/1999 | Herrmann et al. |
| 6,017,318 A | 1/2000 | Gauthier et al. |
| 6,019,747 A | 2/2000 | McPhee |
| 6,023,251 A | 2/2000 | Koo et al. |
| 6,024,539 A | 2/2000 | Blomquist |
| 6,027,826 A | 2/2000 | Derochemont et al. |
| 6,028,568 A | 2/2000 | Asakura et al. |
| 6,031,445 A | 2/2000 | Marty et al. |
| 6,032,059 A | 2/2000 | Henning et al. |
| 6,036,924 A | 3/2000 | Simons et al. |
| 6,040,578 A | 3/2000 | Malin et al. |
| 6,040,805 A | 3/2000 | Huynh et al. |
| 6,046,707 A | 4/2000 | Gaughan et al. |
| 6,049,727 A | 4/2000 | Crothall |
| 6,050,978 A | 4/2000 | Orr et al. |
| 6,052,040 A | 4/2000 | Hino |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,111,544 A | 8/2000 | Dakeya et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |
| 6,128,519 A | 10/2000 | Say |
| 6,142,939 A | 11/2000 | Eppstein et al. |
| 6,143,164 A | 11/2000 | Heller et al. |
| 6,143,432 A | 11/2000 | De et al. |
| 6,154,176 A | 11/2000 | Fathy et al. |
| 6,157,041 A | 12/2000 | Thomas et al. |
| 6,161,028 A | 12/2000 | Braig et al. |
| 6,162,639 A | 12/2000 | Douglas |
| 6,174,300 B1 | 1/2001 | Kriesel et al. |
| 6,176,004 B1 | 1/2001 | Rainhart et al. |
| 6,181,297 B1 | 1/2001 | Leisten |
| 6,188,368 B1 | 2/2001 | Koriyama et al. |
| 6,190,359 B1 | 2/2001 | Heruth |
| 6,195,049 B1 | 2/2001 | Kim et al. |
| 6,196,046 B1 | 3/2001 | Braig et al. |
| 6,200,287 B1 | 3/2001 | Keller et al. |
| 6,200,293 B1 | 3/2001 | Kriesel et al. |
| 6,200,338 B1 | 3/2001 | Solomon et al. |
| 6,204,203 B1 | 3/2001 | Narwankar et al. |
| 6,208,843 B1 | 3/2001 | Huang et al. |
| 6,214,629 B1 | 4/2001 | Freitag et al. |
| 6,222,489 B1 | 4/2001 | Tsuru et al. |
| 6,226,082 B1 | 5/2001 | Roe |
| 6,244,776 B1 | 6/2001 | Wiley |
| 6,261,065 B1 | 7/2001 | Nayak et al. |
| 6,262,798 B1 | 7/2001 | Shepherd et al. |
| 6,266,020 B1 | 7/2001 | Chang |
| 6,270,455 B1 | 8/2001 | Brown |
| 6,271,045 B1 | 8/2001 | Douglas et al. |
| 6,280,381 B1 | 8/2001 | Malin et al. |
| 6,285,448 B1 | 9/2001 | Kuenstner |
| 6,300,894 B1 | 10/2001 | Lynch et al. |

(56) References Cited

U.S. PATENT DOCUMENTS

| | | |
|---|---|---|
| 6,309,370 B1 | 10/2001 | Ben-Haim et al. |
| 6,312,888 B1 | 11/2001 | Wong et al. |
| 6,320,547 B1 | 11/2001 | Fathy et al. |
| 6,323,549 B1 | 11/2001 | Derochemont et al. |
| 6,334,851 B1 | 1/2002 | Hayes et al. |
| 6,363,609 B1 | 4/2002 | Pickren |
| 6,375,627 B1 | 4/2002 | Mauze et al. |
| 6,375,638 B2 | 4/2002 | Nason et al. |
| 6,379,301 B1 | 4/2002 | Worthington et al. |
| 6,402,689 B1 | 6/2002 | Scarantino et al. |
| 6,413,244 B1 | 7/2002 | Bestetti et al. |
| 6,470,279 B1 | 10/2002 | Samsoondar |
| 6,474,219 B2 | 11/2002 | Klitmose et al. |
| 6,475,196 B1 | 11/2002 | Vachon |
| 6,477,065 B2 | 11/2002 | Parks |
| 6,477,901 B1 | 11/2002 | Tadigadapa et al. |
| 6,484,044 B1 | 11/2002 | Lilienfeld-Toal |
| 6,485,461 B1 | 11/2002 | Mason et al. |
| 6,485,462 B1 | 11/2002 | Kriesel |
| 6,491,656 B1 | 12/2002 | Morris |
| 6,492,949 B1 | 12/2002 | Breglia et al. |
| 6,496,149 B1 | 12/2002 | Birnbaum et al. |
| 6,501,415 B1 | 12/2002 | Viana et al. |
| 6,512,937 B2 | 1/2003 | Blank et al. |
| 6,520,936 B1 | 2/2003 | Mann |
| 6,525,509 B1 | 2/2003 | Petersson et al. |
| 6,527,744 B1 | 3/2003 | Kriesel et al. |
| 6,528,809 B1 | 3/2003 | Thomas et al. |
| 6,537,249 B2 | 3/2003 | Kriesell et al. |
| 6,540,260 B1 | 4/2003 | Tan |
| 6,540,672 B1 | 4/2003 | Simonsen et al. |
| 6,541,820 B1 | 4/2003 | Bol |
| 6,544,212 B2 | 4/2003 | Galley et al. |
| 6,546,268 B1 | 4/2003 | Ishikawa et al. |
| 6,546,269 B1 | 4/2003 | Kurnik |
| 6,551,276 B1 | 4/2003 | Mann et al. |
| 6,552,693 B1 | 4/2003 | Leisten |
| 6,553,841 B1 | 4/2003 | Blouch |
| 6,554,798 B1 | 4/2003 | Mann et al. |
| 6,556,850 B1 | 4/2003 | Braig et al. |
| D474,778 S | 5/2003 | Barnes |
| 6,558,351 B1 | 5/2003 | Steil et al. |
| 6,559,735 B1 | 5/2003 | Hoang et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,115 B1 | 5/2003 | Barker et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,583,699 B2 | 6/2003 | Yokoyama |
| 6,595,956 B1 | 7/2003 | Gross et al. |
| 6,599,281 B1 | 7/2003 | Struys et al. |
| 6,605,072 B2 | 8/2003 | Struys et al. |
| 6,611,419 B1 | 8/2003 | Chakravorty |
| 6,618,603 B2 | 9/2003 | Varalli et al. |
| 6,620,750 B2 | 9/2003 | Kim et al. |
| 6,633,772 B2 | 10/2003 | Ford et al. |
| 6,635,958 B2 | 10/2003 | Bates et al. |
| 6,639,556 B2 | 10/2003 | Baba |
| 6,642,908 B2 | 11/2003 | Pleva et al. |
| 6,645,142 B2 | 11/2003 | Braig et al. |
| 6,648,821 B2 | 11/2003 | Lebel et al. |
| 6,650,303 B2 | 11/2003 | Kim et al. |
| 6,653,091 B1 | 11/2003 | Dunn et al. |
| 6,656,158 B2 | 12/2003 | Mahoney et al. |
| 6,662,030 B2 | 12/2003 | Khalil et al. |
| 6,669,663 B1 | 12/2003 | Thompson |
| 6,670,497 B2 | 12/2003 | Tashino et al. |
| 6,678,542 B2 | 1/2004 | Braig et al. |
| 6,680,700 B2 | 1/2004 | Hilgers |
| 6,683,576 B2 | 1/2004 | Achim |
| 6,686,406 B2 | 2/2004 | Tomomatsu et al. |
| 6,690,336 B1 | 2/2004 | Leisten et al. |
| 6,697,605 B1 | 2/2004 | Atokawa et al. |
| 6,699,218 B2 | 3/2004 | Flaherty et al. |
| 6,699,221 B2 | 3/2004 | Vaillancourt |
| 6,718,189 B2 | 4/2004 | Rohrscheib et al. |
| 6,720,926 B2 | 4/2004 | Killen et al. |
| 6,721,582 B2 | 4/2004 | Trepagnier et al. |
| 6,723,072 B2 | 4/2004 | Flaherty et al. |
| 6,727,785 B2 | 4/2004 | Killen et al. |
| 6,728,560 B2 | 4/2004 | Kollias et al. |
| 6,731,244 B2 | 5/2004 | Killen et al. |
| 6,731,248 B2 | 5/2004 | Killen et al. |
| 6,733,890 B2 | 5/2004 | Imanaka et al. |
| 6,740,059 B2 | 5/2004 | Flaherty |
| 6,740,072 B2 | 5/2004 | Starkweather et al. |
| 6,741,148 B2 | 5/2004 | Killen et al. |
| 6,742,249 B2 | 6/2004 | Derochemont et al. |
| 6,743,744 B1 | 6/2004 | Kim et al. |
| 6,750,740 B2 | 6/2004 | Killen et al. |
| 6,750,820 B2 | 6/2004 | Killen et al. |
| 6,751,490 B2 | 6/2004 | Esenaliev et al. |
| 6,753,745 B2 | 6/2004 | Killen et al. |
| 6,753,814 B2 | 6/2004 | Killen et al. |
| 6,758,835 B2 | 7/2004 | Close et al. |
| 6,762,237 B2 | 7/2004 | Glatkowski et al. |
| 6,780,156 B2 | 8/2004 | Haueter et al. |
| 6,787,181 B2 | 9/2004 | Uchiyama et al. |
| 6,791,496 B1 | 9/2004 | Killen et al. |
| 6,799,149 B2 | 9/2004 | Hartlaub |
| 6,810,290 B2 | 10/2004 | Lebel et al. |
| 6,826,031 B2 | 11/2004 | Nagai et al. |
| 6,827,702 B2 | 12/2004 | Lebel et al. |
| 6,830,623 B2 | 12/2004 | Hayashi et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,853,288 B2 | 2/2005 | Ahn et al. |
| 6,858,892 B2 | 2/2005 | Yamagata |
| 6,862,534 B2 | 3/2005 | Sterling et al. |
| 6,864,848 B2 | 3/2005 | Sievenpiper |
| 6,865,408 B1 | 3/2005 | Abbink et al. |
| 6,871,396 B2 | 3/2005 | Sugaya et al. |
| 6,872,200 B2 | 3/2005 | Mann et al. |
| 6,873,268 B2 | 3/2005 | Lebel et al. |
| 6,878,871 B2 | 4/2005 | Scher et al. |
| 6,883,778 B1 | 4/2005 | Newton et al. |
| 6,890,291 B2 | 5/2005 | Robinson et al. |
| 6,905,989 B2 | 6/2005 | Ellis et al. |
| 6,906,674 B2 | 6/2005 | McKinzie et al. |
| 6,914,566 B2 | 7/2005 | Beard |
| 6,919,119 B2 | 7/2005 | Kalkan et al. |
| 6,928,298 B2 | 8/2005 | Furutani et al. |
| 6,936,029 B2 | 8/2005 | Mann et al. |
| 6,943,430 B2 | 9/2005 | Kwon |
| 6,943,731 B2 | 9/2005 | Killen et al. |
| 6,949,081 B1 | 9/2005 | Chance |
| 6,958,809 B2 | 10/2005 | Sterling et al. |
| 6,963,259 B2 | 11/2005 | Killen et al. |
| 6,979,326 B2 | 12/2005 | Mann et al. |
| 6,989,891 B2 | 1/2006 | Braig et al. |
| 6,990,366 B2 | 1/2006 | Say et al. |
| 6,997,920 B2 | 2/2006 | Mann et al. |
| 7,002,436 B2 | 2/2006 | Ma et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis et al. |
| 7,047,637 B2 | 5/2006 | Derochemont et al. |
| 7,060,059 B2 | 6/2006 | Keith et al. |
| 7,060,350 B2 | 6/2006 | Takaya et al. |
| 7,061,593 B2 | 6/2006 | Braig et al. |
| 7,066,910 B2 | 6/2006 | Bauhahn et al. |
| 7,096,124 B2 | 8/2006 | Sterling et al. |

(56) References Cited

U.S. PATENT DOCUMENTS

| | | |
|---|---|---|
| 7,109,878 B2 | 9/2006 | Mann et al. |
| 7,115,205 B2 | 10/2006 | Robinson et al. |
| 7,116,949 B2 | 10/2006 | Irie et al. |
| 7,128,727 B2 | 10/2006 | Flaherty et al. |
| 7,133,329 B2 | 11/2006 | Skyggebjerg et al. |
| 7,137,694 B2 | 11/2006 | Ferran et al. |
| 7,139,593 B2 | 11/2006 | Kavak et al. |
| 7,139,598 B2 | 11/2006 | Hull et al. |
| 7,144,384 B2 | 12/2006 | Gorman et al. |
| 7,160,272 B1 | 1/2007 | Eyal et al. |
| 7,171,252 B1 | 1/2007 | Scarantino et al. |
| 7,179,226 B2 | 2/2007 | Crothall et al. |
| 7,190,988 B2 | 3/2007 | Say et al. |
| 7,220,240 B2 | 5/2007 | Struys et al. |
| 7,230,316 B2 | 6/2007 | Yamazaki et al. |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,291,782 B2 | 11/2007 | Sager et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,405,698 B2 | 7/2008 | De Rochemont |
| 7,429,255 B2 | 9/2008 | Thompson |
| 7,460,130 B2 | 12/2008 | Salganicoff |
| 7,481,787 B2 | 1/2009 | Gable et al. |
| 7,491,187 B2 | 2/2009 | Van et al. |
| 7,500,949 B2 | 3/2009 | Gottlieb et al. |
| 7,509,156 B2 | 3/2009 | Flanders |
| D590,415 S | 4/2009 | Ball et al. |
| 7,522,124 B2 | 4/2009 | Smith et al. |
| 7,547,281 B2 | 6/2009 | Hayes et al. |
| 7,553,512 B2 | 6/2009 | Kodas et al. |
| 7,564,887 B2 | 7/2009 | Wang et al. |
| 7,569,030 B2 | 8/2009 | Lebel et al. |
| 7,595,623 B2 | 9/2009 | Bennett |
| 7,608,042 B2 | 10/2009 | Goldberger et al. |
| 7,651,845 B2 | 1/2010 | Doyle et al. |
| 7,652,901 B2 | 1/2010 | Kirchmeier et al. |
| 7,680,529 B2 | 3/2010 | Kroll |
| D614,634 S | 4/2010 | Nilsen |
| 7,704,226 B2 | 4/2010 | Mueller et al. |
| 7,714,794 B2 | 5/2010 | Tavassoli Hozouri |
| 7,734,323 B2 | 6/2010 | Blomquist et al. |
| 7,763,917 B2 | 7/2010 | De Rochemont |
| 7,766,829 B2 | 8/2010 | Sloan et al. |
| 7,771,391 B2 | 8/2010 | Carter |
| 7,785,258 B2 | 8/2010 | Braig et al. |
| 7,785,313 B2 | 8/2010 | Mastrototaro |
| 7,806,853 B2 | 10/2010 | Wittmann et al. |
| 7,806,854 B2 | 10/2010 | Damiano et al. |
| 7,806,886 B2 | 10/2010 | Kanderian et al. |
| 7,812,774 B2 | 10/2010 | Friman et al. |
| 7,815,602 B2 | 10/2010 | Mann et al. |
| 7,819,843 B2 | 10/2010 | Mann et al. |
| 7,850,641 B2 | 12/2010 | Lebel et al. |
| 7,918,825 B2 | 4/2011 | O'Connor et al. |
| 7,946,985 B2 | 5/2011 | Mastrototaro et al. |
| D640,269 S | 6/2011 | Chen |
| 7,967,812 B2 | 6/2011 | Jasperson et al. |
| 7,972,296 B2 | 7/2011 | Braig et al. |
| 7,976,492 B2 | 7/2011 | Brauker et al. |
| 8,062,249 B2 | 11/2011 | Wilinska et al. |
| 8,066,805 B2 | 11/2011 | Zuercher et al. |
| 8,069,690 B2 | 12/2011 | Desantolo et al. |
| 8,088,098 B2 | 1/2012 | Yodfat et al. |
| 8,105,268 B2 | 1/2012 | Lebel et al. |
| 8,114,489 B2 | 2/2012 | Nemat-Nasser et al. |
| 8,152,789 B2 | 4/2012 | Starkweather et al. |
| 8,178,457 B2 | 5/2012 | De Rochemont |
| 8,193,873 B2 | 6/2012 | Kato et al. |
| 8,206,350 B2 | 6/2012 | Mann et al. |
| 8,208,984 B2 | 6/2012 | Blomquist et al. |
| 8,221,345 B2 | 7/2012 | Blomquist |
| 8,226,556 B2 | 7/2012 | Hayes et al. |
| 8,251,907 B2 | 8/2012 | Sterling et al. |
| 8,267,893 B2 | 9/2012 | Moberg et al. |
| 8,267,921 B2 | 9/2012 | Yodfat et al. |
| 8,273,052 B2 | 9/2012 | Damiano et al. |
| 8,350,657 B2 | 1/2013 | Derochemont |
| 8,352,011 B2 | 1/2013 | Van et al. |
| 8,354,294 B2 | 1/2013 | De et al. |
| D677,685 S | 3/2013 | Simmons et al. |
| 8,417,311 B2 | 4/2013 | Rule |
| 8,439,834 B2 | 5/2013 | Schmelzeisen-Redeker et al. |
| 8,439,897 B2 | 5/2013 | Yodfat et al. |
| 8,449,524 B2 | 5/2013 | Braig et al. |
| 8,452,359 B2 | 5/2013 | Rebec et al. |
| 8,454,576 B2 | 6/2013 | Mastrototaro et al. |
| 8,460,231 B2 | 6/2013 | Brauker et al. |
| 8,467,980 B2 | 6/2013 | Campbell et al. |
| 8,478,557 B2 | 7/2013 | Hayter et al. |
| 8,480,655 B2 | 7/2013 | Jasperson et al. |
| D688,686 S | 8/2013 | Rhee et al. |
| 8,547,239 B2 | 10/2013 | Peatfield et al. |
| 8,548,544 B2 | 10/2013 | Kircher et al. |
| 8,551,045 B2 | 10/2013 | Sie et al. |
| 8,560,082 B2 | 10/2013 | Wei |
| 8,560,131 B2 | 10/2013 | Haueter et al. |
| 8,562,587 B2 | 10/2013 | Kovatchev et al. |
| D693,837 S | 11/2013 | Bouchier |
| 8,579,879 B2 | 11/2013 | Palerm et al. |
| 8,585,591 B2 | 11/2013 | Sloan et al. |
| 8,585,637 B2 | 11/2013 | Wilinska et al. |
| 8,585,638 B2 | 11/2013 | Blomquist |
| 8,593,819 B2 | 11/2013 | De Rochemont |
| D695,757 S | 12/2013 | Ray et al. |
| 8,597,274 B2 | 12/2013 | Sloan et al. |
| 8,615,366 B2 | 12/2013 | Galley et al. |
| 8,622,988 B2 | 1/2014 | Hayter |
| 8,694,115 B2 | 4/2014 | Goetz et al. |
| 8,706,691 B2 | 4/2014 | McDaniel et al. |
| 8,715,839 B2 | 5/2014 | De Rochemont |
| 8,718,949 B2 | 5/2014 | Blomquist et al. |
| 8,721,585 B2 | 5/2014 | Brauker et al. |
| 8,727,982 B2 | 5/2014 | Jennewine |
| 8,734,428 B2 | 5/2014 | Blomquist |
| 8,747,315 B2 | 6/2014 | Brauker et al. |
| 8,756,043 B2 | 6/2014 | Albisser et al. |
| 8,768,673 B2 | 7/2014 | Albisser et al. |
| 8,777,896 B2 | 7/2014 | Starkweather et al. |
| 8,784,369 B2 | 7/2014 | Starkweather et al. |
| 8,784,370 B2 | 7/2014 | Lebel et al. |
| D710,879 S | 8/2014 | Elston et al. |
| 8,795,224 B2 | 8/2014 | Starkweather et al. |
| 8,810,394 B2 | 8/2014 | Kalpin |
| D714,822 S | 10/2014 | Capua et al. |
| D715,315 S | 10/2014 | Wood |
| D715,815 S | 10/2014 | Bortman et al. |
| 8,876,755 B2 | 11/2014 | Taub et al. |
| D718,779 S | 12/2014 | Hang et al. |
| D720,366 S | 12/2014 | Hiltunen et al. |
| D720,765 S | 1/2015 | Xie et al. |
| 8,939,935 B2 | 1/2015 | O'Connor et al. |
| 8,977,504 B2 | 3/2015 | Hovorka |
| 8,992,475 B2 | 3/2015 | Mann et al. |
| D726,760 S | 4/2015 | Yokota et al. |
| D727,928 S | 4/2015 | Allison et al. |
| D730,378 S | 5/2015 | Xiong et al. |
| D733,175 S | 6/2015 | Bae |
| 9,061,097 B2 | 6/2015 | Holt et al. |
| D734,356 S | 7/2015 | Xiong et al. |
| D736,811 S | 8/2015 | Teichner et al. |
| D737,305 S | 8/2015 | Scazafavo et al. |
| D737,831 S | 9/2015 | Lee |
| D737,832 S | 9/2015 | Lim et al. |
| D738,901 S | 9/2015 | Amin |

(56) References Cited

U.S. PATENT DOCUMENTS

| | | |
|---|---|---|
| D740,301 S | 10/2015 | Soegiono et al. |
| D740,308 S | 10/2015 | Kim et al. |
| D740,311 S | 10/2015 | Drozd et al. |
| D741,354 S | 10/2015 | Lee et al. |
| D741,359 S | 10/2015 | Ji-Hye et al. |
| 9,171,343 B1 | 10/2015 | Fischell et al. |
| D743,431 S | 11/2015 | Pal et al. |
| D743,991 S | 11/2015 | Pal et al. |
| 9,180,224 B2 | 11/2015 | Moseley et al. |
| 9,180,244 B2 | 11/2015 | Anderson et al. |
| 9,192,716 B2 | 11/2015 | Jugl et al. |
| D744,514 S | 12/2015 | Shin et al. |
| D744,517 S | 12/2015 | Pal et al. |
| D745,032 S | 12/2015 | Pal et al. |
| D745,034 S | 12/2015 | Pal et al. |
| D745,035 S | 12/2015 | Pal et al. |
| D746,827 S | 1/2016 | Jung et al. |
| D746,828 S | 1/2016 | Arai et al. |
| D747,352 S | 1/2016 | Lee et al. |
| 9,233,204 B2 | 1/2016 | Booth et al. |
| D749,097 S | 2/2016 | Zou et al. |
| D749,118 S | 2/2016 | Wang |
| D751,100 S | 3/2016 | Lindn et al. |
| D752,604 S | 3/2016 | Zhang |
| D753,134 S | 4/2016 | Vazquez |
| D754,718 S | 4/2016 | Zhou |
| 9,320,471 B2 | 4/2016 | Hayes et al. |
| D755,193 S | 5/2016 | Sun et al. |
| D755,799 S | 5/2016 | Finnis et al. |
| D755,820 S | 5/2016 | Wang |
| D756,387 S | 5/2016 | Chang et al. |
| D757,032 S | 5/2016 | Sabia et al. |
| D757,035 S | 5/2016 | Raskin et al. |
| 9,333,298 B2 | 5/2016 | Kim et al. |
| D758,391 S | 6/2016 | Suarez |
| D758,422 S | 6/2016 | Zhao |
| D759,032 S | 6/2016 | Amin et al. |
| D759,078 S | 6/2016 | Iwamoto |
| D759,678 S | 6/2016 | Jung et al. |
| D759,687 S | 6/2016 | Chang et al. |
| D761,812 S | 7/2016 | Motamedi |
| D763,308 S | 8/2016 | Wang et al. |
| D763,868 S | 8/2016 | Lee et al. |
| D765,110 S | 8/2016 | Liang |
| D765,124 S | 8/2016 | Minks-Brown et al. |
| 9,402,950 B2 | 8/2016 | Dilanni et al. |
| 9,415,157 B2 | 8/2016 | Mann et al. |
| D765,707 S | 9/2016 | Gomez |
| D766,286 S | 9/2016 | Lee et al. |
| D767,586 S | 9/2016 | Kwon et al. |
| D768,154 S | 10/2016 | Kim et al. |
| D768,188 S | 10/2016 | Li et al. |
| D768,660 S | 10/2016 | Wielgosz |
| D768,685 S | 10/2016 | Lee et al. |
| D769,315 S | 10/2016 | Scotti |
| 9,474,855 B2 | 10/2016 | McCann et al. |
| D770,507 S | 11/2016 | Umezawa et al. |
| D770,515 S | 11/2016 | Cho et al. |
| D771,073 S | 11/2016 | Choi et al. |
| D771,076 S | 11/2016 | Butcher et al. |
| D771,690 S | 11/2016 | Yin et al. |
| D772,911 S | 11/2016 | Lee et al. |
| 9,480,796 B2 | 11/2016 | Starkweather et al. |
| 9,486,172 B2 | 11/2016 | Cobelli et al. |
| 9,486,571 B2 | 11/2016 | Rosinko |
| 9,486,578 B2 | 11/2016 | Finan et al. |
| D773,531 S | 12/2016 | Toth et al. |
| D775,184 S | 12/2016 | Song et al. |
| D775,196 S | 12/2016 | Huang et al. |
| 9,520,649 B2 | 12/2016 | De Rochemont |
| D775,658 S | 1/2017 | Luo et al. |
| D776,126 S | 1/2017 | Lai et al. |
| D776,687 S | 1/2017 | Wick et al. |
| D777,191 S | 1/2017 | Polimeni |
| D777,758 S | 1/2017 | Kisselev et al. |
| 9,579,456 B2 | 2/2017 | Budiman et al. |
| D781,323 S | 3/2017 | Green et al. |
| D781,781 S | 3/2017 | Schimmoeller, Jr. |
| D781,877 S | 3/2017 | Ko et al. |
| D781,878 S | 3/2017 | Butcher et al. |
| D781,879 S | 3/2017 | Butcher et al. |
| D781,903 S | 3/2017 | Reichle et al. |
| D781,905 S | 3/2017 | Nakaguchi et al. |
| D782,506 S | 3/2017 | Kim et al. |
| D783,672 S | 4/2017 | Rajasankar et al. |
| D785,010 S | 4/2017 | Bachman et al. |
| D785,656 S | 5/2017 | Bramer et al. |
| D786,278 S | 5/2017 | Motamedi |
| D786,898 S | 5/2017 | Hall |
| D788,126 S | 5/2017 | Evnin et al. |
| 9,656,017 B2 | 5/2017 | Greene |
| D788,621 S | 6/2017 | Shallice et al. |
| D788,652 S | 6/2017 | Mutsuro et al. |
| D789,402 S | 6/2017 | Dye et al. |
| D789,967 S | 6/2017 | Kaplan et al. |
| D789,982 S | 6/2017 | Christiana et al. |
| D790,560 S | 6/2017 | Inose et al. |
| D791,781 S | 7/2017 | Donarski et al. |
| D791,805 S | 7/2017 | Segars |
| D791,812 S | 7/2017 | Bistoni et al. |
| D793,412 S | 8/2017 | Chaudhri et al. |
| D795,886 S | 8/2017 | Ng et al. |
| D795,891 S | 8/2017 | Kohan et al. |
| D795,900 S | 8/2017 | Bischoff et al. |
| D795,906 S | 8/2017 | Butrick |
| D795,927 S | 8/2017 | Bischoff et al. |
| 9,743,224 B2 | 8/2017 | San et al. |
| D796,530 S | 9/2017 | McMillan et al. |
| D796,540 S | 9/2017 | McLean et al. |
| D797,116 S | 9/2017 | Chapman et al. |
| D797,763 S | 9/2017 | Kim et al. |
| D797,774 S | 9/2017 | Park et al. |
| D797,797 S | 9/2017 | Gandhi et al. |
| D798,310 S | 9/2017 | Golden et al. |
| D798,311 S | 9/2017 | Golden et al. |
| D799,536 S | 10/2017 | Eder |
| D800,765 S | 10/2017 | Stoksik |
| D800,769 S | 10/2017 | Hennessy et al. |
| D801,383 S | 10/2017 | Park et al. |
| D802,011 S | 11/2017 | Friedman et al. |
| D802,088 S | 11/2017 | Bos et al. |
| D803,232 S | 11/2017 | Leigh et al. |
| D803,242 S | 11/2017 | Mizono et al. |
| D804,502 S | 12/2017 | Amini et al. |
| D805,525 S | 12/2017 | Dascola et al. |
| D806,716 S | 1/2018 | Pahwa et al. |
| D807,376 S | 1/2018 | Mizono et al. |
| D807,400 S | 1/2018 | Lagreca |
| D807,910 S | 1/2018 | Graham et al. |
| D807,918 S | 1/2018 | Cohen et al. |
| D807,919 S | 1/2018 | Cohen et al. |
| D808,423 S | 1/2018 | Jiang et al. |
| D808,974 S | 1/2018 | Chiappone et al. |
| D808,983 S | 1/2018 | Narinedhat et al. |
| 9,857,090 B2 | 1/2018 | Golden et al. |
| D810,116 S | 2/2018 | McLean et al. |
| D810,771 S | 2/2018 | Gandhi et al. |
| 9,907,515 B2 | 3/2018 | Doyle et al. |
| D815,131 S | 4/2018 | Thompson et al. |
| D816,090 S | 4/2018 | Stonecipher et al. |
| D817,339 S | 5/2018 | Nanjappan et al. |
| D818,491 S | 5/2018 | Timmer et al. |
| D819,057 S | 5/2018 | Huang |
| D819,059 S | 5/2018 | O'Toole |
| 9,980,140 B1 | 5/2018 | Spencer et al. |
| 9,984,773 B2 | 5/2018 | Gondhalekar et al. |
| D820,311 S | 6/2018 | Cabrera et al. |
| D820,862 S | 6/2018 | Alfonzo et al. |
| D822,034 S | 7/2018 | Clymer et al. |
| D822,677 S | 7/2018 | Weaver et al. |
| D822,684 S | 7/2018 | Clausen-Stuck et al. |
| D822,692 S | 7/2018 | Loychik et al. |
| D823,862 S | 7/2018 | Chung et al. |
| D824,400 S | 7/2018 | Chang et al. |

(56) References Cited

U.S. PATENT DOCUMENTS

| | | |
|---|---|---|
| D824,951 S | 8/2018 | Kolbrener et al. |
| D826,956 S | 8/2018 | Pillalamarri et al. |
| D826,957 S | 8/2018 | Pillalamarri et al. |
| D828,381 S | 9/2018 | Lee et al. |
| D829,732 S | 10/2018 | Jeffrey et al. |
| D830,374 S | 10/2018 | Leonard et al. |
| D830,384 S | 10/2018 | Lepine et al. |
| D830,385 S | 10/2018 | Lepine et al. |
| D830,407 S | 10/2018 | Kisielius et al. |
| D831,033 S | 10/2018 | Leonard et al. |
| 10,102,344 B2 | 10/2018 | Rees et al. |
| D833,469 S | 11/2018 | Coleman et al. |
| D834,601 S | 11/2018 | Felt |
| D835,132 S | 12/2018 | Ito et al. |
| D835,145 S | 12/2018 | Cashner et al. |
| D835,147 S | 12/2018 | Kisielius et al. |
| D835,651 S | 12/2018 | Bao |
| D835,666 S | 12/2018 | Saleh et al. |
| D836,123 S | 12/2018 | Pillalamarri et al. |
| D837,807 S | 1/2019 | Baber et al. |
| D838,731 S | 1/2019 | Pillalamarri et al. |
| D840,418 S | 2/2019 | Saad et al. |
| D840,419 S | 2/2019 | Saad et al. |
| 10,195,343 B2 | 2/2019 | Kamen et al. |
| D844,022 S | 3/2019 | Amin |
| D845,317 S | 4/2019 | Wellmeier et al. |
| 10,248,839 B2 | 4/2019 | Levy et al. |
| D848,459 S | 5/2019 | Li |
| D851,099 S | 6/2019 | Uppala et al. |
| D851,658 S | 6/2019 | Pillalamarri et al. |
| 10,307,538 B2 | 6/2019 | Desborough et al. |
| 10,335,464 B1 | 7/2019 | Michelich et al. |
| 10,391,242 B2 | 8/2019 | Agrawal et al. |
| D865,795 S | 11/2019 | Koo |
| 10,500,334 B2 | 12/2019 | Mazlish et al. |
| D872,746 S | 1/2020 | Laborde |
| D874,471 S | 2/2020 | Pillalamarri et al. |
| D875,114 S | 2/2020 | Clediere |
| 10,583,250 B2 | 3/2020 | Mazlish et al. |
| D880,498 S | 4/2020 | Shahidi et al. |
| 10,610,644 B2 | 4/2020 | Mazlish et al. |
| D888,070 S | 6/2020 | Yusupov et al. |
| 10,737,024 B2 | 8/2020 | Schmid |
| D904,426 S | 12/2020 | Debashish |
| 10,881,793 B2 | 1/2021 | Mazlish et al. |
| D911,353 S | 2/2021 | Sanchez et al. |
| D914,031 S | 3/2021 | Ding et al. |
| D916,729 S | 4/2021 | Gabriel et al. |
| D916,870 S | 4/2021 | Hemsley |
| D916,878 S | 4/2021 | Kim et al. |
| 10,987,468 B2 | 4/2021 | Mazlish et al. |
| D918,261 S | 5/2021 | Ramamurthy et al. |
| D920,351 S | 5/2021 | Zhang |
| D923,033 S | 6/2021 | Smith et al. |
| 11,027,063 B2 | 6/2021 | Mazlish et al. |
| 11,033,682 B2 * | 6/2021 | Mazlish ................ G16H 20/17 |
| D927,533 S | 8/2021 | Clymer |
| 11,116,900 B2 | 9/2021 | Haider et al. |
| D938,447 S | 12/2021 | Holland |
| 11,197,964 B2 | 12/2021 | Sjolund et al. |
| 11,260,169 B2 | 3/2022 | Estes |
| 11,309,089 B2 | 4/2022 | Kahlbaugh |
| D954,078 S | 6/2022 | Rahate et al. |
| 2001/0021803 A1 | 9/2001 | Blank et al. |
| 2001/0034023 A1 | 10/2001 | Stanton et al. |
| 2001/0034502 A1 | 10/2001 | Moberg et al. |
| 2001/0048969 A1 | 12/2001 | Constantino et al. |
| 2001/0051377 A1 | 12/2001 | Hammer et al. |
| 2001/0053895 A1 | 12/2001 | Vaillancourt |
| 2001/0056258 A1 | 12/2001 | Evans |
| 2002/0010401 A1 | 1/2002 | Bushmakin et al. |
| 2002/0010423 A1 | 1/2002 | Gross et al. |
| 2002/0016568 A1 | 2/2002 | Lebel et al. |
| 2002/0040208 A1 | 4/2002 | Flaherty et al. |
| 2002/0047768 A1 | 4/2002 | Duffy |
| 2002/0070983 A1 | 6/2002 | Kozub et al. |
| 2002/0123740 A1 | 9/2002 | Flaherty et al. |
| 2002/0128543 A1 | 9/2002 | Leonhardt |
| 2002/0147423 A1 | 10/2002 | Burbank et al. |
| 2002/0155425 A1 | 10/2002 | Han et al. |
| 2002/0161288 A1 | 10/2002 | Shin et al. |
| 2002/0173769 A1 | 11/2002 | Gray et al. |
| 2002/0190818 A1 | 12/2002 | Endou et al. |
| 2003/0023148 A1 | 1/2003 | Lorenz et al. |
| 2003/0023152 A1 | 1/2003 | Abbink et al. |
| 2003/0034124 A1 | 2/2003 | Sugaya et al. |
| 2003/0040715 A1 | 2/2003 | D'Antonio et al. |
| 2003/0050621 A1 | 3/2003 | Lebel et al. |
| 2003/0060692 A1 | 3/2003 | Ruchti et al. |
| 2003/0060765 A1 | 3/2003 | Campbell et al. |
| 2003/0086073 A1 | 5/2003 | Braig et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0100040 A1 | 5/2003 | Bonnecaze et al. |
| 2003/0114836 A1 | 6/2003 | Estes et al. |
| 2003/0122647 A1 | 7/2003 | Ou |
| 2003/0130616 A1 | 7/2003 | Steil et al. |
| 2003/0135388 A1 | 7/2003 | Martucci et al. |
| 2003/0144582 A1 | 7/2003 | Cohen et al. |
| 2003/0148024 A1 | 8/2003 | Kodas et al. |
| 2003/0163097 A1 | 8/2003 | Fleury et al. |
| 2003/0170436 A1 | 9/2003 | Sumi et al. |
| 2003/0175806 A1 | 9/2003 | Rule et al. |
| 2003/0195404 A1 | 10/2003 | Knobbe et al. |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2003/0220605 A1 | 11/2003 | Bowman et al. |
| 2003/0221621 A1 | 12/2003 | Pokharna et al. |
| 2004/0001027 A1 | 1/2004 | Killen et al. |
| 2004/0010207 A1 | 1/2004 | Flaherty et al. |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064088 A1 | 4/2004 | Gorman et al. |
| 2004/0064259 A1 | 4/2004 | Haaland et al. |
| 2004/0068224 A1 | 4/2004 | Couvillon et al. |
| 2004/0069004 A1 | 4/2004 | Gist et al. |
| 2004/0069044 A1 | 4/2004 | Lavi et al. |
| 2004/0087904 A1 | 5/2004 | Langley et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Inoue et al. |
| 2005/0022274 A1 | 1/2005 | Campbell et al. |
| 2005/0033148 A1 | 2/2005 | Haueter et al. |
| 2005/0043598 A1 | 2/2005 | Goode et al. |
| 2005/0049179 A1 | 3/2005 | Davidson et al. |
| 2005/0065464 A1 | 3/2005 | Talbot et al. |
| 2005/0065465 A1 | 3/2005 | Lebel et al. |
| 2005/0075624 A1 | 4/2005 | Miesel |
| 2005/0105095 A1 | 5/2005 | Pesach et al. |
| 2005/0134609 A1 | 6/2005 | Yu |
| 2005/0137573 A1 | 6/2005 | McLaughlin |
| 2005/0171503 A1 | 8/2005 | Van et al. |
| 2005/0177398 A1 | 8/2005 | Watanabe et al. |
| 2005/0182306 A1 | 8/2005 | Sloan |
| 2005/0182366 A1 | 8/2005 | Vogt et al. |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |

(56) References Cited

U.S. PATENT DOCUMENTS

| | | |
|---|---|---|
| 2005/0203461 A1 | 9/2005 | Flaherty et al. |
| 2005/0238507 A1 | 10/2005 | Diianni et al. |
| 2005/0261660 A1 | 11/2005 | Choi |
| 2005/0262451 A1 | 11/2005 | Remignanti et al. |
| 2005/0272640 A1 | 12/2005 | Doyle et al. |
| 2005/0277912 A1 | 12/2005 | John |
| 2006/0009727 A1 | 1/2006 | O'Mahony et al. |
| 2006/0041229 A1 | 2/2006 | Garibotto et al. |
| 2006/0064053 A1 | 3/2006 | Bollish et al. |
| 2006/0079765 A1 | 4/2006 | Neer et al. |
| 2006/0079809 A1 | 4/2006 | Goldberger et al. |
| 2006/0086994 A1 | 4/2006 | Viefers et al. |
| 2006/0100494 A1 | 5/2006 | Kroll |
| 2006/0134323 A1 | 6/2006 | O'Brien |
| 2006/0134491 A1 | 6/2006 | Hilchenko et al. |
| 2006/0167350 A1 | 7/2006 | Monfre et al. |
| 2006/0173406 A1 | 8/2006 | Hayes et al. |
| 2006/0178633 A1 | 8/2006 | Garibotto et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253067 A1 | 11/2006 | Staib et al. |
| 2006/0253085 A1 | 11/2006 | Geismar et al. |
| 2006/0264895 A1 | 11/2006 | Flanders |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0083160 A1 | 4/2007 | Hall et al. |
| 2007/0100635 A1 | 5/2007 | Mahajan et al. |
| 2007/0106135 A1 | 5/2007 | Sloan et al. |
| 2007/0116601 A1 | 5/2007 | Patton |
| 2007/0118405 A1 | 5/2007 | Campbell et al. |
| 2007/0129690 A1 | 6/2007 | Rosenblatt et al. |
| 2007/0142720 A1 | 6/2007 | Ridder et al. |
| 2007/0166453 A1 | 7/2007 | Van et al. |
| 2007/0173761 A1 | 7/2007 | Kanderian et al. |
| 2007/0173974 A1 | 7/2007 | Lin |
| 2007/0179352 A1 | 8/2007 | Randlov et al. |
| 2007/0191716 A1 | 8/2007 | Goldberger et al. |
| 2007/0197163 A1 | 8/2007 | Robertson |
| 2007/0225675 A1 | 9/2007 | Robinson et al. |
| 2007/0244381 A1 | 10/2007 | Robinson et al. |
| 2007/0249007 A1 | 10/2007 | Rosero |
| 2007/0259768 A1 | 11/2007 | Kear et al. |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0033272 A1 | 2/2008 | Gough et al. |
| 2008/0033320 A1 | 2/2008 | Racchini et al. |
| 2008/0051738 A1 | 2/2008 | Griffin |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0078400 A1 | 4/2008 | Martens et al. |
| 2008/0097289 A1 | 4/2008 | Steil et al. |
| 2008/0114304 A1 | 5/2008 | Nalesso et al. |
| 2008/0132880 A1 | 6/2008 | Buchman |
| 2008/0160492 A1 | 7/2008 | Campbell et al. |
| 2008/0161664 A1 | 7/2008 | Mastrototaro et al. |
| 2008/0172026 A1 | 7/2008 | Blomquist |
| 2008/0172028 A1 | 7/2008 | Blomquist |
| 2008/0177165 A1 | 7/2008 | Blomquist et al. |
| 2008/0183060 A1 | 7/2008 | Steil et al. |
| 2008/0188796 A1 | 8/2008 | Steil et al. |
| 2008/0200838 A1 | 8/2008 | Goldberger et al. |
| 2008/0206067 A1 | 8/2008 | De et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287906 A1 | 11/2008 | Burkholz et al. |
| 2008/0300572 A1 | 12/2008 | Rankers et al. |
| 2009/0006061 A1 | 1/2009 | Thukral et al. |
| 2009/0018406 A1 | 1/2009 | Yodfat et al. |
| 2009/0030398 A1 | 1/2009 | Yodfat et al. |
| 2009/0036753 A1 | 2/2009 | King |
| 2009/0043240 A1 | 2/2009 | Robinson et al. |
| 2009/0054753 A1 | 2/2009 | Robinson et al. |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0131861 A1 | 5/2009 | Braig et al. |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0164239 A1 | 6/2009 | Hayter et al. |
| 2009/0164251 A1 | 6/2009 | Hayter |
| 2009/0198350 A1 | 8/2009 | Thiele |
| 2009/0212966 A1 | 8/2009 | Panduro |
| 2009/0221890 A1 | 9/2009 | Saffer et al. |
| 2009/0228214 A1 | 9/2009 | Say et al. |
| 2009/0318791 A1 | 12/2009 | Kaastrup |
| 2009/0326343 A1 | 12/2009 | Gable et al. |
| 2009/0326472 A1 | 12/2009 | Carter et al. |
| 2010/0017141 A1 | 1/2010 | Campbell et al. |
| 2010/0036326 A1 | 2/2010 | Matusch |
| 2010/0049164 A1 | 2/2010 | Estes |
| 2010/0057042 A1 | 3/2010 | Hayter |
| 2010/0064243 A1 | 3/2010 | Buck et al. |
| 2010/0077198 A1 | 3/2010 | Buck et al. |
| 2010/0114026 A1 | 5/2010 | Karratt et al. |
| 2010/0121170 A1 | 5/2010 | Rule |
| 2010/0125241 A1 | 5/2010 | Prud et al. |
| 2010/0137784 A1 | 6/2010 | Cefai et al. |
| 2010/0137788 A1 | 6/2010 | Braithwaite et al. |
| 2010/0138197 A1 | 6/2010 | Sher |
| 2010/0145272 A1 | 6/2010 | Cefai et al. |
| 2010/0152658 A1 | 6/2010 | Hanson et al. |
| 2010/0174228 A1 | 7/2010 | Buckingham et al. |
| 2010/0185183 A1 | 7/2010 | Alme et al. |
| 2010/0211003 A1 | 8/2010 | Sundar et al. |
| 2010/0228110 A1 | 9/2010 | Tsoukalis |
| 2010/0241066 A1 | 9/2010 | Hansen et al. |
| 2010/0249561 A1 | 9/2010 | Patek et al. |
| 2010/0256466 A1 | 10/2010 | Shekalim et al. |
| 2010/0262117 A1 | 10/2010 | Magni et al. |
| 2010/0262434 A1 | 10/2010 | Shaya |
| 2010/0292634 A1 | 11/2010 | Kircher et al. |
| 2010/0295686 A1 | 11/2010 | Sloan et al. |
| 2010/0298765 A1 | 11/2010 | Budiman et al. |
| 2011/0015511 A1 | 1/2011 | Bousamra et al. |
| 2011/0021584 A1 | 1/2011 | Berggren et al. |
| 2011/0028817 A1 | 2/2011 | Jin et al. |
| 2011/0049394 A1 | 3/2011 | De Rochemont |
| 2011/0054390 A1 | 3/2011 | Searle et al. |
| 2011/0054399 A1 | 3/2011 | Chong et al. |
| 2011/0065224 A1 | 3/2011 | Bollman et al. |
| 2011/0071765 A1 | 3/2011 | Yodfat et al. |
| 2011/0124996 A1 | 5/2011 | Reinke et al. |
| 2011/0144586 A1 | 6/2011 | Michaud et al. |
| 2011/0160652 A1 | 6/2011 | Yodfat et al. |
| 2011/0178472 A1 | 7/2011 | Cabiri |
| 2011/0190694 A1 | 8/2011 | Lanier et al. |
| 2011/0202005 A1 | 8/2011 | Yodfat et al. |
| 2011/0205065 A1 | 8/2011 | Strachan et al. |
| 2011/0208156 A1 | 8/2011 | Doyle et al. |
| 2011/0218495 A1 | 9/2011 | Remde |
| 2011/0230833 A1 | 9/2011 | Landman et al. |
| 2011/0251509 A1 | 10/2011 | Beyhan et al. |
| 2011/0282320 A1 | 11/2011 | Steil et al. |

(56) References Cited

U.S. PATENT DOCUMENTS

| | | |
|---|---|---|
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0030393 A1 | 2/2012 | Ganesh et al. |
| 2012/0053556 A1 | 3/2012 | Lee |
| 2012/0059351 A1 | 3/2012 | Nordh |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0124521 A1 | 5/2012 | Guo |
| 2012/0136336 A1 | 5/2012 | Mastrototaro et al. |
| 2012/0150446 A1 | 6/2012 | Chang et al. |
| 2012/0172694 A1 | 7/2012 | Desborough et al. |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |
| 2012/0226259 A1 | 9/2012 | Yodfat et al. |
| 2012/0227737 A1 | 9/2012 | Mastrototaro et al. |
| 2012/0232520 A1 | 9/2012 | Sloan et al. |
| 2012/0238851 A1 | 9/2012 | Kamen et al. |
| 2012/0245556 A1 | 9/2012 | Kovatchev et al. |
| 2012/0246106 A1 | 9/2012 | Atlas et al. |
| 2012/0246406 A1 | 9/2012 | Bell et al. |
| 2012/0250449 A1 | 10/2012 | Nakano |
| 2012/0271655 A1 | 10/2012 | Knobel et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2013/0030358 A1 | 1/2013 | Yodfat et al. |
| 2013/0102867 A1 | 4/2013 | Desborough et al. |
| 2013/0158503 A1 | 6/2013 | Kanderian et al. |
| 2013/0172695 A1 | 7/2013 | Nielsen et al. |
| 2013/0172710 A1 | 7/2013 | Mears et al. |
| 2013/0178791 A1 | 7/2013 | Javitt |
| 2013/0231642 A1 | 9/2013 | Doyle et al. |
| 2013/0245545 A1 | 9/2013 | Arnold et al. |
| 2013/0245547 A1 | 9/2013 | El-Khatib et al. |
| 2013/0253472 A1 | 9/2013 | Cabiri |
| 2013/0261406 A1 | 10/2013 | Rebec et al. |
| 2013/0296792 A1 | 11/2013 | Cabiri |
| 2013/0296823 A1 | 11/2013 | Melker et al. |
| 2013/0298080 A1 | 11/2013 | Griffin et al. |
| 2013/0317753 A1 | 11/2013 | Kamen et al. |
| 2013/0332874 A1 | 12/2013 | Rosinko et al. |
| 2013/0338576 A1 | 12/2013 | O'Connor et al. |
| 2013/0338629 A1 | 12/2013 | Agrawal et al. |
| 2013/0338630 A1 | 12/2013 | Agrawal et al. |
| 2013/0346858 A1 | 12/2013 | Neyrinck |
| 2014/0005633 A1 | 1/2014 | Finan |
| 2014/0018730 A1 | 1/2014 | Mueller-Pathle |
| 2014/0032549 A1 | 1/2014 | McDaniel et al. |
| 2014/0066859 A1 | 3/2014 | Ogawa et al. |
| 2014/0066884 A1 | 3/2014 | Keenan et al. |
| 2014/0066886 A1 | 3/2014 | Roy et al. |
| 2014/0066887 A1 | 3/2014 | Mastrototaro et al. |
| 2014/0066888 A1 | 3/2014 | Parikh et al. |
| 2014/0066889 A1 | 3/2014 | Grosman et al. |
| 2014/0074033 A1 | 3/2014 | Sonderegger et al. |
| 2014/0088428 A1 | 3/2014 | Yang et al. |
| 2014/0108046 A1 | 4/2014 | Echeverria et al. |
| 2014/0121635 A1 | 5/2014 | Hayter |
| 2014/0127048 A1 | 5/2014 | Diianni et al. |
| 2014/0128839 A1 | 5/2014 | Diianni et al. |
| 2014/0129951 A1 | 5/2014 | Amin et al. |
| 2014/0135880 A1 | 5/2014 | Baumgartner et al. |
| 2014/0142508 A1 | 5/2014 | Diianni et al. |
| 2014/0146202 A1 | 5/2014 | Boss et al. |
| 2014/0171901 A1 | 6/2014 | Langsdorf et al. |
| 2014/0180203 A1 | 6/2014 | Budiman et al. |
| 2014/0180240 A1 | 6/2014 | Finan et al. |
| 2014/0188072 A1 | 7/2014 | Rinehart et al. |
| 2014/0200426 A1 | 7/2014 | Taub et al. |
| 2014/0200559 A1 | 7/2014 | Doyle et al. |
| 2014/0230021 A1 | 8/2014 | Birtwhistle et al. |
| 2014/0276553 A1 | 9/2014 | Rosinko et al. |
| 2014/0276554 A1 | 9/2014 | Finan et al. |
| 2014/0276555 A1 | 9/2014 | Morales |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2014/0350369 A1 | 11/2014 | Budiman et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0025503 A1 | 1/2015 | Searle et al. |
| 2015/0041498 A1 | 2/2015 | Kakiuchi et al. |
| 2015/0045767 A1 | 2/2015 | Kamen et al. |
| 2015/0073337 A1 | 3/2015 | Saint et al. |
| 2015/0120317 A1 | 4/2015 | Mayou et al. |
| 2015/0134265 A1 | 5/2015 | Kohlbrecher et al. |
| 2015/0134353 A1 | 5/2015 | Ferrell et al. |
| 2015/0164343 A1 | 6/2015 | Huang et al. |
| 2015/0165117 A1 | 6/2015 | Palerm et al. |
| 2015/0165119 A1 | 6/2015 | Palerm et al. |
| 2015/0173674 A1 | 6/2015 | Hayes et al. |
| 2015/0193585 A1 | 7/2015 | Sunna |
| 2015/0202386 A1 | 7/2015 | Brady et al. |
| 2015/0205509 A1 | 7/2015 | Scriven et al. |
| 2015/0205511 A1 | 7/2015 | Vinna et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0238694 A1 | 8/2015 | Steil et al. |
| 2015/0265767 A1 | 9/2015 | Vazquez et al. |
| 2015/0289821 A1 | 10/2015 | Rack-Gomer et al. |
| 2015/0289823 A1 | 10/2015 | Rack-Gomer et al. |
| 2015/0301691 A1 | 10/2015 | Qin |
| 2015/0306312 A1 | 10/2015 | Palerm |
| 2015/0306314 A1 | 10/2015 | Doyle et al. |
| 2015/0314062 A1 | 11/2015 | Blomquist et al. |
| 2015/0328402 A1 | 11/2015 | Nogueira et al. |
| 2015/0331995 A1 | 11/2015 | Zhao et al. |
| 2015/0351671 A1 | 12/2015 | Vanslyke et al. |
| 2015/0351672 A1 | 12/2015 | Vanslyke et al. |
| 2015/0356250 A1 | 12/2015 | Polimeni |
| 2015/0366945 A1 | 12/2015 | Greene |
| 2016/0015891 A1 | 1/2016 | Papiorek |
| 2016/0019352 A1 | 1/2016 | Cohen et al. |
| 2016/0030669 A1 | 2/2016 | Harris et al. |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0082188 A1 | 3/2016 | Blomquist et al. |
| 2016/0089494 A1 | 3/2016 | Guerrini |
| 2016/0158438 A1 | 6/2016 | Monirabbasi et al. |
| 2016/0162662 A1 | 6/2016 | Monirabbasi et al. |
| 2016/0175520 A1 | 6/2016 | Palerm et al. |
| 2016/0213841 A1 | 7/2016 | Geismar et al. |
| 2016/0220181 A1 | 8/2016 | Rigoard et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0256629 A1 | 9/2016 | Grosman et al. |
| 2016/0259889 A1 | 9/2016 | Murtha et al. |
| 2016/0287512 A1 | 10/2016 | Cooper et al. |
| 2016/0302054 A1 | 10/2016 | Kimura et al. |
| 2016/0317743 A1 | 11/2016 | Estes |
| 2016/0331310 A1 | 11/2016 | Kovatchev |
| 2016/0354543 A1 | 12/2016 | Cinar et al. |
| 2017/0007882 A1 | 1/2017 | Werner |
| 2017/0021096 A1 | 1/2017 | Cole et al. |
| 2017/0049386 A1 | 2/2017 | Abraham et al. |
| 2017/0131887 A1 | 5/2017 | Kim et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |

(56) References Cited

U.S. PATENT DOCUMENTS

| | | |
|---|---|---|
| 2017/0173261 A1 | 6/2017 | O'Connor et al. |
| 2017/0182248 A1 | 6/2017 | Rosinko |
| 2017/0188943 A1 | 7/2017 | Braig et al. |
| 2017/0189625 A1 | 7/2017 | Cirillo et al. |
| 2017/0203038 A1 | 7/2017 | Desborough et al. |
| 2017/0216524 A1 | 8/2017 | Haider et al. |
| 2017/0232195 A1 | 8/2017 | Desborough et al. |
| 2017/0239415 A1 | 8/2017 | Hwang et al. |
| 2017/0258987 A1 | 9/2017 | Caspers |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0332952 A1 | 11/2017 | Desborough et al. |
| 2017/0347971 A1 | 12/2017 | Davis et al. |
| 2017/0348482 A1 | 12/2017 | Duke et al. |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | Ambrsio |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200436 A1 | 7/2018 | Mazlish et al. |
| 2018/0200438 A1 | 7/2018 | Mazlish et al. |
| 2018/0200440 A1 | 7/2018 | Mazlish et al. |
| 2018/0200441 A1 | 7/2018 | Desborough et al. |
| 2018/0204636 A1 | 7/2018 | Edwards et al. |
| 2018/0277253 A1 | 9/2018 | Gondhalekar et al. |
| 2018/0289891 A1 | 10/2018 | Finan et al. |
| 2018/0296757 A1 | 10/2018 | Finan et al. |
| 2018/0307515 A1 | 10/2018 | Meller et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0095052 A1 | 3/2019 | De et al. |
| 2019/0132801 A1 | 5/2019 | Kamath et al. |
| 2019/0184091 A1 | 6/2019 | Sjolund et al. |
| 2019/0240403 A1 | 8/2019 | Palerm et al. |
| 2019/0290844 A1 | 9/2019 | Monirabbasi et al. |
| 2019/0321545 A1 | 10/2019 | Saint |
| 2019/0336683 A1 | 11/2019 | O'Connor et al. |
| 2019/0336684 A1 | 11/2019 | O'Connor et al. |
| 2019/0348157 A1 | 11/2019 | Booth et al. |
| 2019/0374714 A1 | 12/2019 | Rioux et al. |
| 2020/0001006 A1 | 1/2020 | Pizzochero et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1 | 4/2020 | O'Connor et al. |
| 2020/0113515 A1 | 4/2020 | O'Connor et al. |
| 2020/0219625 A1 | 7/2020 | Kahlbaugh |
| 2020/0342974 A1 | 10/2020 | Chen et al. |
| 2021/0050085 A1 | 2/2021 | Hayter et al. |
| 2021/0098105 A1 | 4/2021 | Lee et al. |
| 2022/0023536 A1 | 1/2022 | Graham et al. |
| 2022/0105270 A1 | 4/2022 | Doyle et al. |

FOREIGN PATENT DOCUMENTS

| | | |
|---|---|---|
| AU | 2015301146 A1 | 3/2017 |
| CA | 1040271 A | 10/1978 |
| CA | 3026851 A1 | 2/2020 |
| CN | 1297140 A | 5/2001 |
| CN | 101010676 A | 8/2007 |
| CN | 101208699 A | 6/2008 |
| CN | 102500013 A | 6/2012 |
| CN | 102596307 A | 7/2012 |
| CN | 103400028 A | 11/2013 |
| CN | 103418053 A | 12/2013 |
| CN | 103907116 A | 7/2014 |
| CN | 104769595 A | 7/2015 |
| CN | 104837517 A | 8/2015 |
| CN | 105452866 A | 3/2016 |
| DE | 4200595 A1 | 7/1993 |
| DE | 19756872 A1 | 7/1999 |
| EP | 0026056 A1 | 4/1981 |
| EP | 0341049 A2 | 11/1989 |
| EP | 0496305 A2 | 7/1992 |
| EP | 0549341 A1 | 6/1993 |
| EP | 0867196 A2 | 9/1998 |
| EP | 0939451 A1 | 9/1999 |
| EP | 1376759 A2 | 1/2004 |
| EP | 1177802 B1 | 9/2004 |
| EP | 1491144 A1 | 12/2004 |
| EP | 1498067 A1 | 1/2005 |
| EP | 1571582 A2 | 9/2005 |
| EP | 0801578 B1 | 7/2006 |
| EP | 2139382 A1 | 1/2010 |
| EP | 2397181 A1 | 12/2011 |
| EP | 2468338 A1 | 6/2012 |
| EP | 2666520 A1 | 11/2013 |
| EP | 2695573 A2 | 2/2014 |
| EP | 2703024 A1 | 3/2014 |
| EP | 2830499 A1 | 2/2015 |
| EP | 2897071 A1 | 7/2015 |
| EP | 2943149 A1 | 11/2015 |
| EP | 2967450 | 1/2016 |
| EP | 3177344 A1 | 6/2017 |
| EP | 3193979 A1 | 7/2017 |
| EP | 3314548 A1 | 5/2018 |
| EP | 3607985 A1 | 2/2020 |
| FR | 2096275 A5 | 2/1972 |
| GB | 1125897 A | 9/1968 |
| GB | 2443261 A | 4/2008 |
| JP | 51-125993 A | 11/1976 |
| JP | 02-131777 A | 5/1990 |
| JP | 2004-283378 A | 10/2004 |
| JP | 2005-326943 A | 11/2005 |
| JP | 2007-525276 A | 9/2007 |
| JP | 2008-513142 A | 5/2008 |
| JP | 2008-545454 A | 12/2008 |
| JP | 2010-523167 A | 7/2010 |
| JP | 2010-531678 A | 9/2010 |
| JP | 2012-516735 A | 7/2012 |
| JP | 2012-527981 A | 11/2012 |
| JP | 2017-516548 A | 6/2017 |
| JP | 2017-525451 A | 9/2017 |
| JP | 2018-153569 A | 10/2018 |
| JP | 2019-525276 A | 9/2019 |
| TW | 200740148 A | 10/2007 |
| TW | M452390 U | 5/2013 |
| WO | 86/06796 A1 | 11/1986 |
| WO | 98/00193 A1 | 1/1998 |
| WO | 98/55073 A1 | 12/1998 |
| WO | 99/10040 A1 | 3/1999 |
| WO | 99/10049 A1 | 3/1999 |
| WO | 99/56803 A1 | 11/1999 |
| WO | 99/62576 A1 | 12/1999 |
| WO | 00/30705 A1 | 6/2000 |
| WO | 00/32258 A1 | 6/2000 |
| WO | 00/48112 A2 | 8/2000 |
| WO | 01/72354 A2 | 10/2001 |
| WO | 01/78812 A1 | 10/2001 |
| WO | 02/15954 A1 | 2/2002 |
| WO | 02/26282 A2 | 4/2002 |
| WO | 02/43866 A2 | 6/2002 |
| WO | 02/76535 A1 | 10/2002 |
| WO | 02/82990 A1 | 10/2002 |
| WO | 03/16882 A1 | 2/2003 |
| WO | 03/39362 A1 | 5/2003 |
| WO | 03/45233 A1 | 6/2003 |
| WO | 03/97133 A1 | 11/2003 |
| WO | 2004/043250 A1 | 5/2004 |
| WO | 2004/092715 A1 | 10/2004 |
| WO | 2005/051170 A2 | 6/2005 |
| WO | 2005/082436 A1 | 9/2005 |
| WO | 2005/110601 A1 | 11/2005 |
| WO | 2005/113036 A1 | 12/2005 |
| WO | 2006/021430 A2 | 3/2006 |
| WO | 2006/053007 A2 | 5/2006 |
| WO | 2006/124716 A3 | 3/2007 |
| WO | 2007/064835 A2 | 6/2007 |

(56) References Cited

FOREIGN PATENT DOCUMENTS

| | | |
|---|---|---|
| WO | 2007/066152 A2 | 6/2007 |
| WO | 2007/078937 A2 | 7/2007 |
| WO | 2008/024810 A2 | 2/2008 |
| WO | 2008/029403 A1 | 3/2008 |
| WO | 2008/057384 A3 | 9/2008 |
| WO | 2008/133702 A1 | 11/2008 |
| WO | 2008/157780 A1 | 12/2008 |
| WO | 2009/023407 A1 | 2/2009 |
| WO | 2009/039203 A2 | 3/2009 |
| WO | 2009/045462 A1 | 3/2009 |
| WO | 2009/049252 A1 | 4/2009 |
| WO | 2009/066287 A2 | 5/2009 |
| WO | 2009/066288 A1 | 5/2009 |
| WO | 2009/098648 A2 | 8/2009 |
| WO | 2009/134380 A2 | 11/2009 |
| WO | 2009/146119 A2 | 12/2009 |
| WO | 2010/022069 A2 | 2/2010 |
| WO | 2010/053702 A1 | 5/2010 |
| WO | 2010/077279 A1 | 7/2010 |
| WO | 2010/089307 A1 | 8/2010 |
| WO | 2010/132077 A1 | 11/2010 |
| WO | 2010/138848 A1 | 12/2010 |
| WO | 2010/139793 A1 | 12/2010 |
| WO | 2010/147659 A2 | 12/2010 |
| WO | 2011/030343 A1 | 3/2011 |
| WO | 2011/031458 A1 | 3/2011 |
| WO | 2011/075042 A1 | 6/2011 |
| WO | 2011/095483 A1 | 8/2011 |
| WO | 2011/133823 A1 | 10/2011 |
| WO | 2012/006208 A2 | 1/2012 |
| WO | 2012/045667 A2 | 4/2012 |
| WO | 2012/073032 A1 | 6/2012 |
| WO | 2012/108959 A1 | 8/2012 |
| WO | 2012/134588 A1 | 10/2012 |
| WO | 2012/177353 A1 | 12/2012 |
| WO | 2012/178134 A2 | 12/2012 |
| WO | 2013/050535 A2 | 4/2013 |
| WO | 2013/078200 A1 | 5/2013 |
| WO | 2013/134486 A2 | 9/2013 |
| WO | 2013/149186 A1 | 10/2013 |
| WO | 2013/177565 A1 | 11/2013 |
| WO | 2013/182321 A1 | 12/2013 |
| WO | 2014/029416 A1 | 2/2014 |
| WO | 2014/035672 A2 | 3/2014 |
| WO | 2014/109898 A1 | 7/2014 |
| WO | 2014/110538 A1 | 7/2014 |
| WO | 2014/149357 A1 | 9/2014 |
| WO | 2014/149535 A1 | 9/2014 |
| WO | 2014/179774 A1 | 11/2014 |
| WO | 2014/194183 A2 | 12/2014 |
| WO | 2015/056259 A1 | 4/2015 |
| WO | 2015/061493 A1 | 4/2015 |
| WO | 2015/073211 A1 | 5/2015 |
| WO | 2015/081337 A2 | 6/2015 |
| WO | 2015/117082 A1 | 8/2015 |
| WO | 2015/117854 A1 | 8/2015 |
| WO | 2015/167201 A1 | 11/2015 |
| WO | 2015/177082 A1 | 11/2015 |
| WO | 2015/187366 A1 | 12/2015 |
| WO | 2015/187738 A1 | 12/2015 |
| WO | 2016/004088 A1 | 1/2016 |
| WO | 2016/022650 A1 | 2/2016 |
| WO | 2016/041873 A1 | 3/2016 |
| WO | 2016/089702 A1 | 6/2016 |
| WO | 2016/141082 A1 | 9/2016 |
| WO | 2016/161254 A1 | 10/2016 |
| WO | 2017/004278 A1 | 1/2017 |
| WO | 2017/027459 A1 | 2/2017 |
| WO | 2017/091624 A1 | 6/2017 |
| WO | 2017/105600 A1 | 6/2017 |
| WO | 2017/124006 A1 | 7/2017 |
| WO | 2017/184988 A1 | 10/2017 |
| WO | 2017/187177 A1 | 11/2017 |
| WO | 2017/205816 A1 | 11/2017 |
| WO | 2018/009614 A1 | 1/2018 |
| WO | 2018/067748 A1 | 4/2018 |
| WO | 2018/120104 A1 | 7/2018 |
| WO | 2018/136799 A1 | 7/2018 |
| WO | 2018/204568 A1 | 11/2018 |
| WO | 2019/077482 A1 | 4/2019 |
| WO | 2019/094440 A1 | 5/2019 |
| WO | 2019/213493 A1 | 11/2019 |
| WO | 2019/246381 A1 | 12/2019 |
| WO | 2020/081393 A1 | 4/2020 |
| WO | 2021/011738 A1 | 1/2021 |

OTHER PUBLICATIONS

Dassau and Associates, 12-Week 24/7 Ambulatory Artificial Pancreas With Weekly Adaptation of Insulin Delivery Settings: Effect on Hemoglobin A1C and Hypoglycemia, Diabetes Care, Oct. 13, 2017.
David A. Copp, Ravi Gondhalekar, and Joao P. Hespanha, Simultaneous Model Predictive Control and Moving Horizon Estimation for Blood Glucose Regulation in Type 1 Diabetes, Optimal Control Applications and Methods, Wiley InterScience, DOI: 10.1002/oca, pp. 1-15, Oct. 2016.
Dunn et al. Development of the Likelihood of Low Glucose (LLG) Algorithm for Evaluating Risk of Hypoglycemia: A New Approach for Using Continuous Glucose Data to Guide Therapeutic Decision Making. Journal of Diabetes and Science Technology. 2014, vol. 8, No. 4, pp. 720-730 (Year: 2014).
E. Salzsieder, G. Albrecht, E. Jutzi, and U. Fischer, Estimation of Individually Adapted Control Parameters for an Artificial Beta Cell, Biomedica Biochimica Acta. 43(5) pp. 585-596, May 1984.
Fischer et al., In Vivo Comparison of Different Algorithms for the Artificial Beta-Cell, Artificial Organs, 9(2), International Society for Artificial Organs, May 1985, New York.
Guy A. Dumont, Feedback Control for Clinicians, Springer Science+ Media, Apr. 12, 2013, New York.
Michele Schiavon, Chiara Dalla Man, Yogish C. Kudva, Ananda Basu, and Claudio Cobelli, Quantitative Estimation of Insulin Sensitivity in Type 1 Diabetic Subjects Wearing a Sensor-Augmented Insulin Pump, Diabetes Care, vol. 37, pp. 1216-1223, May 2014.
Samuel Vozeh and Jean-Louis Steimer, Feedback Control Methods for Drug Dosage Optimisation, Concepts, Classification and Clinical Application, Clinical Pharmacokinetics, 10(6), pp. 457-476, Nov.-Dec. 1985.
Anonymous: "Insulin pump", Wikipedia, Dec. 11, 2011 (Dec. 11, 2011), XP055192359.
Anonymous: "Super Bolus – This is Caleb…", Apr. 21, 2010 (Apr. 21, 2010), XP055689518.
Canadian Examination Report for Canadian Patent Application No. 3,009,351, dated Jan. 27, 2023, 6 pages.
Canadian Examination Report for Canadian Patent Application No. 3,009,831, dated Aug. 18, 2022, 4 pages.
Chinese Decision of Rejection for Chinese Patent Application No. 202110390474.7, dated May 10, 2023, 10 pages with translation.
European Communication pursuant to Article 94(3) EPC for European Application No. 17739083.8, dated Aug. 3, 2021, 5 pages.
European Communication pursuant to Article 94(3) EPC for European Application No. 17803425, dated Feb. 20, 2023, 5 pages.
European Communication pursuant to Article 94(3) EPC for European Application No. 18178056.0, dated Dec. 23, 2022, 5 pages.
European Communication pursuant to Article 94(3) EPC for European Application No. 18178057.8, dated Jan. 24, 2023, 5 pages.
European Communication pursuant to Article 94(3) EPC for European Application No. 18702853.5, dated Jul. 13, 2022, 4 pages.
European Communication pursuant to Article 94(3) EPC for European Application No. 18702854.3, dated Jun. 6, 2022, 5 pages.
European Communication pursuant to Article 94(3) EPC for European Application No. 18703123.2, dated Jul. 6, 2022, 6 pages.
European Communication pursuant to Article 94(3) EPC for European Application No. 18709156.6, dated Sep. 14, 2022, 4 pages.
Examination Report for Chinese Application No. 202110390473.7, dated Dec. 27, 2022, 15 pages with translation.

(56) References Cited

OTHER PUBLICATIONS

Japanese Reasons for Refusal from Japanese Application No. 2021-073220, dated Jan. 18, 2022, 8 pages.
Search Report and Written Opinion of the International Searching Authority, as issued in connection with the International Patent Application No. PCT/US17/34012 dated Aug. 17, 2017, 8 pages.
Third Party Observations for European Application No. 18702854.3, dated Jan. 24, 2023, 6 pages.
Wang et al., "Automatic Bolus and Adaptive Basal Algorithm for the Artificial Pancreatic β-Cell," Diabetes Technology & Therapeutics, vol. 12, No. 11, (2010), 11 pages.
Parker, R.S., Doyle, F.J. and Peppas, N.A., 2001. The intravenous route to blood glucose control. IEEE Engineering in Medicine and Biology Magazine, 20(1), pp. 65-73. (Year: 2001).
Patek, S.D., Magni, L., Dassau, E., Karvetski, C., Toffanin, C., De Nicolao, G., Del Favero, S., Breton, M., Dalla Man, C., Renard, E. and Zisser, H., 2012. Modular closed-loop control of diabetes. IEEE Transactions on Biomedical Engineering, 59(11), pp. 2986-2999. (Year: 2012).
Trevitt, S., Simpson, S. and Wood, A, 2016. Artificial pancreas device systems for the closed-loop control of type 1 diabetes: what systems are in development?. Journal of diabetes science and technology, 10(3), pp. 714-723. (Year: 2016).

\* cited by examiner

INSULIN DELIVERY METHODS, SYSTEMS AND DEVICES

CROSS-REFERENCE TO RELATED APPLICATIONS

This application is a continuation of U.S. patent application Ser. No. 15/870,717, filed Jan. 12, 2018, now U.S. Pat. No. 11,033,682, issued Jun. 15, 2021, which application claims the benefit under 35 U.S.C. § 119(e) of U.S. Provisional Patent Application Ser. No. 62/563,804, filed Sep. 27, 2017, for "INSULIN DELIVERY METHODS, SYSTEMS AND DEVICES," U.S. Provisional Patent Application Ser. No. 62/563,836, filed Sep. 27, 2017, for "INSULIN DELIVERY METHODS, SYSTEMS AND DEVICES," and U.S. Provisional Patent Application Ser. No. 62/446,236, filed Jan. 13, 2017, "SYSTEM AND METHOD FOR ADJUSTING INSULIN DELIVERY," the disclosure of each of which is hereby incorporated herein in its entirety by this reference.

TECHNICAL FIELD

The disclosure relates to constraints on insulin delivery and/or alarms and/or alerts based insulin delivery data.

BACKGROUND

People with Type I, Type II, or gestational diabetes must track their blood glucose levels and sometimes treat their condition to maintain appropriate blood glucose levels. Control of diabetes can include the monitoring of blood glucose levels using a variety of devices. Examples of such devices include blood glucose monitors (BGMs), continuous glucose monitors (CGMs), and sometimes flash glucose monitors (FMs). People with Type I, and some people with Type II or gestational diabetes, require insulin or an analog thereof. Because it cannot be taken orally, insulin is injected with a syringe or delivered subcutaneously by an external infusion pump. However, each person responds to insulin in a slightly different way. Furthermore, blood glucose levels can vary at different times of the day.

In addition to variations in blood glucose levels, other factors associated with the treatment of diabetes can also vary. For example, an insulin sensitivity factor (ISF) and a carbohydrate to insulin ratio (CR) can vary from person to person and at various points in time. To account for such variations, some systems personalize one or more of these factors.

Embodiments of the present disclosure are not limited to embodiments that solve any disadvantages or that operate only in environments such as those described above. Rather, this background is only provided to illustrate one example technology area where some embodiments described in the present disclosure may be practiced.

BRIEF SUMMARY

Medication delivery systems, methods, and devices provided herein include a control device (e.g., controller integrated with an insulin delivery device, a controller removably attachable to an insulin delivery device, smartphone having an installed app, etc.) to personalize insulin delivery for a person with diabetes (PWD). In some cases, methods, devices, and systems provided herein can include an insulin delivery device (e.g., an insulin pump, a smart insulin pen, an insulin pen system including a connected dose-capture cap, etc.) in communication with or part of the blood glucose monitoring device and/or the control device. In some cases, various constraints may be placed on personalization of insulin delivery for the PWD. For example, if the PWD has been receiving an increase from their normal baseline basal rate beyond a certain threshold, the control device may adjust the personalization of insulin delivery and/or return to a nominal or baseline level of insulin delivery. Additionally or alternatively, if the PWD has been receiving a decrease from their normal baseline basal rate beyond another threshold, the control device may adjust the personalization of insulin delivery and/or return to a nominal or baseline level of insulin delivery. Such an adjustment may include delivering the normal baseline basal rate for the PWD, e.g., by exiting a feedback delivery mode (such as a personalized set of delivery actions) to a standard delivery mode (such as delivering the typical baseline basal rate for the PWD).

One or more embodiments may include a method of insulin delivery, the method may include obtaining one or more blood glucose readings of a user, and, based on the blood glucose readings, generating a set of insulin delivery actions that may include delivery of a baseline basal rate or predefined variations of the baseline basal rate. The method may also include monitoring previous insulin delivery actions to the user to determine whether the previous insulin delivery actions include insulin beyond a threshold amount, where the previous insulin delivery actions may include delivery of the baseline basal rate or predefined variations of the baseline basal rate, and, based on the previous insulin delivery actions including insulin beyond the threshold amount, adjusting the set of insulin delivery actions. In some cases, the threshold amount can be based on a calculation of Insulin-on-Board (IOB) ratio, which can be a Total IOB Ratio of Total IOB to Nominal Basal IOB based on all insulin delivered to the PWD or a Basal IOB Ratio of the IOB due to insulin delivered based on variations from a BBR to Nominal Basal IOB. For example, in some cases, methods, devices, and systems provided herein can calculate the Total IOB Ratio and the Basal IOB Ratio, and revert to delivering the BBR (e.g., exit a closed-loop delivery mode) if the Basal IOB Ratio is greater than a threshold (e.g., 1.9, 1.85, 1.8, 1.75, or 1.7) and/or if the Total IOB Ratio is less than a threshold (e.g., 0.5, 0.45, 0.4, 0.35, 0.3, or 0.25). A lower constraint on the Total IOB Ratio can mitigate a risk of a PWD entering diabetic ketoacidosis (DKA), and an upper constraint on the Basal IOB Ratio can mitigate a risk of a PWD receiving too much basal insulin due to inaccurate glucose data.

One or more embodiments may include issuing an alarm or alert to the user when a threshold has caused the system or device provided herein to adjust the personalization of insulin delivery and/or return to a nominal or baseline level of basal insulin delivery. In some embodiments, a system or device can return to a standard delivery mode (e.g., an open-looped mode) and issue an alarm when a threshold has been reached, and require that the user acknowledge the alarm and/or change the delivery mode back to the feedback delivery mode prior to the system or device returning to the feedback delivery mode. In some embodiments, a system or device can simply change the personalization without an associated alarm or alert until the amount of delivered basal is once again within a predetermined range based on one or more thresholds. In some cases, the delivery of basal insulin above an upper threshold can trigger an alarm and/or exit from a feedback mode while the delivery of basal insulin below a lower threshold may simply result in the system delivering a predetermined or baseline amount of insulin for a predetermined period of time while the device or system remains in feedback mode.

Medication delivery systems, methods, and devices provided herein can provide smart alerts or alarms that may be related to an amount of insulin suggested for a correction bolus. For example, if a diabetes management system monitors blood glucose levels and insulin deliveries and determines that a correction bolus is advisable, the diabetes management system may send a message to the user suggesting the use of a correction bolus of insulin to lower the blood glucose level of a PWD. If the suggested correction bolus exceeds a threshold amount, an alert may be provided to the user regarding the amount of insulin suggested in the correction bolus. In some cases, the threshold amount may be a static amount of insulin. In other cases, the threshold amount may be a dynamic amount and the determination of whether an alert should be triggered may be related to an estimated blood glucose level, an amount of insulin on board (IOB) of the PWD, an insulin sensitivity factor (ISF) of the PWD, and/or the total daily basal amount of insulin received by the PWD, or any combinations thereof.

In some cases, the correction bolus may be based on an equation that may include:

$$\frac{EGV - \text{Target}}{ISF} - IOB$$

where estimated blood glucose level (EGV) includes the estimated blood glucose level, Target includes the target blood glucose level, ISF includes the insulin sensitivity factor, and IOB includes the insulin on board. The correction bolus may be compared to a portion of the total daily bolus dose (TDBD) designated for a given diurnal time period. For example, the correction bolus may be compared to the TDBD for one of the twenty-four hours in a day. Stated mathematically, an alert may be triggered when the following inequality is met:

$$\frac{EGV - \text{Target}}{ISF} - IOB \geq \frac{TDBD}{24}$$

In some cases, the portion of TDBD designated for a given diurnal time period may be multiplied by a user-designated factor, such that the alert may trigger more readily (e.g., when the factor is low) or may trigger less readily (e.g., when the factor is high). In some embodiments, the factor may be between approximately 0.5 and 5, for example, 1, 2, 3, or 4. In some cases, other suitable correction bolus equations can be used, which can consider additional user-specific dosage parameters and other physiological information about the PWD (e.g., food or carbohydrates on board, information about exercise, sickness, etc.). In some cases, the threshold for an alert can be based on other or additional user-specific dosage parameters for the PWD (e.g., it can be based on the user's nominal basal rate (BBR) for one or more diurnal time blocks, the PWD's average or time specific ISF, the PWD's average or time specific CR, etc.). In some cases, however calculated, the threshold for triggering an alert or alarm indicating the need to take a correction bolus can reflect that the correction dose is equal to at least 30 minutes of nominal basal insulin, at least 1 hour of nominal basal insulin, at least 2 hours of nominal basal insulin, or at least 3 hours of nominal basal insulin.

One or more embodiments of the present disclosure may include an insulin delivery monitoring system that includes an insulin delivery device configured to deliver insulin to a user, and a controller configured to perform or control performance of operations. The operations may include receiving notification of an amount of insulin delivered by the insulin delivery device, and determining a correction dose based on (1) a variance between an estimated blood glucose level of the user and a target blood glucose level of the user, (2) an insulin sensitivity factor of the user, and (3) an amount of insulin on board (IOB) for the user, where the insulin on board for the user is based at least on the amount of insulin delivered by the insulin delivery device. In some cases, the operations can include determining an IOB due to basal insulin deliveries, bolus insulin deliveries, and/or all insulin deliveries. In some cases, the operations can include a comparison of calculated IOBs to what would be present if the PWD only received nominal basal insulin deliveries. The operations may also include comparing the correction dose with a threshold insulin delivery amount, and, based on the correction dose exceeding the threshold insulin delivery amount, trigger an alarm or alert to the user.

One or more embodiments of the present disclosure may include a method of insulin delivery comprising: obtaining one or more blood glucose readings of a user; based on the blood glucose readings, generating a set of insulin delivery actions, the set of insulin delivery actions including delivery of a baseline basal rate or predefined variations of the baseline basal rate; at least one of monitoring previous insulin delivery actions to the user to determine whether the previous insulin delivery actions include insulin beyond a threshold amount, calculating an amount of basal insulin on board (IOB) due to the insulin delivery actions, or calculating a total IOB due to the previous insulin delivery actions; and based on the previous insulin delivery actions, adjusting the set of insulin delivery actions.

The details of one or more implementations of various embodiments are set forth in the accompanying drawings and the description below. Other features, objects, and advantages of the various embodiments will be apparent from the description and drawings, and from the claims.

It is to be understood that both the foregoing general description and the following detailed description are merely examples and explanatory and are not restrictive of the claims.

BRIEF DESCRIPTION OF THE DRAWINGS

Example embodiments will be described and explained with additional specificity and detail through the use of the accompanying drawings in which.

DETAILED DESCRIPTION

Figure 1:
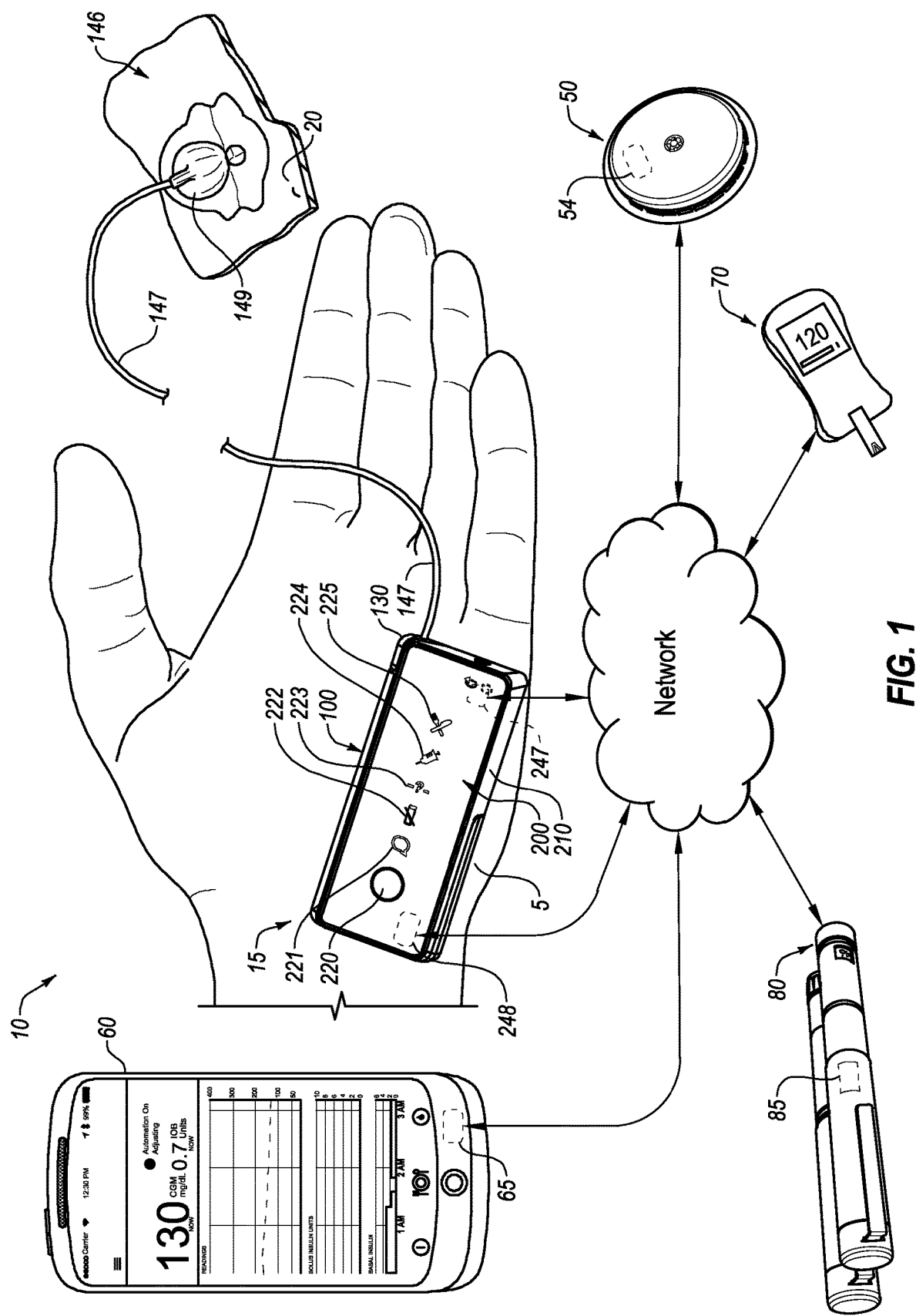
FIG. 1 provides an example system to provide insulin delivery that may be limited by constraints.

The present disclosure may relate to, inter alia, the use of constraints and/or thresholds in the personalized delivery of insulin and/or the issuing of alarms and/or alerts. For example, a control device of an insulin delivery system may control delivery of insulin to a PWD by delivering insulin or generating commands to deliver insulin via a series of delivery actions and/or use insulin data in determining whether to issue an alarm or an alert to a PWD or a caregiver.

Constraints on Insulin Delivery

Insulin delivery devices, systems, and methods provided herein can use any suitable feedback system to modify the delivery of insulin using any suitable control device or mechanism. Any suitable modification of basal rates or the automatic delivery of micro boluses in response to glucose data can be used in method, systems, and devices provided herein. In some embodiments, delivery actions can include predefined variations of the baseline basal rate (BBR) (which may be considered the nominal basal rate) for the PWD to approximate a target blood glucose level. For example, if a PWD was expected to have high blood glucose levels shortly in the future, a series of delivery actions may include 0×, 1×, 2×, 2×, 2×, 2×, 2×, 2× of the BBR for the PWD. As the duration of time that the delivery actions are above the BBR for the PWD, there is a concern that an abnormality may be occurring. For example, the abnormality may include the user making a mistake (e.g., forgetting to take a bolus of insulin for a meal), or it may include the insulin delivery system having a problem (e.g., a CGM or FM is not operating properly), or some other abnormality (e.g., a hacked control device delivering excessive insulin). Because of the risk associated with low blood glucose levels, constraints may be built into the insulin delivery system such that as the delivery actions surpass a threshold (e.g., in number of actions, duration of time with extra insulin, amount of insulin, etc.), the delivery system may revert to delivery of the BBR. This may avoid situations in which a PWD may inadvertently receive too much insulin due to the personalization algorithm repeatedly delivering insulin at a predefined variation above the BBR.

In a similar manner, the present disclosure may relate to a constraint related to the under-delivery of insulin. For example, if a PWD was expected to have low blood glucose levels shortly in the future, a series of delivery actions may include 1×, 0×, 0×, 0×, 0×, 0×, 0×, 0× of the BBR. As the duration of time that the delivery actions are below the BBR for the PWD, there is a concern that an abnormality may be occurring. For example, the abnormality may include the user making a mistake (e.g., not having eaten any carbohydrates for an extended period of time), or it may include the insulin delivery system having a problem (e.g., a CGM or FM is not operating properly), or some other abnormality (e.g., a hacked control device preventing the delivery of insulin). Because of the risk associated with high blood glucose levels and/or the lack of any insulin being in a PWD's system, constraints may be built into the insulin delivery system such that as the delivery actions surpass a threshold (e.g., in number of actions, duration of time without insulin, amount of insulin, etc.), the delivery system may revert to delivery of the BBR or another basal rate that is not based on glucose data. This may avoid situations in which a PWD may inadvertently not receive any (or an insufficient amount of) insulin for an extended period of time due to the personalization algorithm repeatedly delivering insulin at a predefined variation below the BBR. In some cases, the constraints related to ensuring a minimum amount of insulin may also consider whether bolus insulin has been delivered, in addition to whether baseline basal has been delivered. For example, if a set of delivery actions includes 0×, 0×, 0×, 0×, 0×, 0×, 0×, 0×, but the PWD receives a bolus of insulin near the end of the delivery actions, the control system may continue to allow the 0× delivery of insulin because of the bolus of insulin (e.g., because a Total IOB calculation is above a threshold).

Personalizing the delivery of insulin may include any approach of adjusting one or more factors associated with insulin delivery based on properties of the PWD. For example, such personalization may include generating multiple insulin delivery profiles and projected blood glucose levels for each of the insulin delivery profiles, and selecting the profile that closely tracks towards a target blood glucose level. In addition, factors that contribute to the predicted blood glucose levels (e.g., insulin sensitivity factor (ISF), carbohydrate to insulin ratio (CR), etc.) may also be personalized over time. Examples of such personalization are described in greater detail in U.S. patent application Ser. No. 15/601,282, the disclosure of which is hereby incorporated herein in its entirety by this reference.

Methods and systems provided herein can use information from a glucose monitor device to have up-to-date blood glucose data (e.g., multiple blood glucose data points each hour) for the PWD in order to determine how to adjust basal insulin delivery rates (referred to as "baseline basal rate" or BBR). In some cases, methods and systems provided herein can use blood glucose data from an FM, a CGM, and/or one or more BGMs. Methods and systems provided herein can be part of a hybrid closed loop system (for example, where basal rates can be adjusted automatically and the PWD can manually enter or deliver a bolus). In some cases, methods and system provided herein can be part of a fully closed loop system (for example, where basal rates can be adjusted automatically and boluses can be delivered automatically). Such a hybrid closed loop or closed loop system may be referred to as a feedback delivery mode. In some cases, the feedback delivery mode may deliver insulin according to a delivery action that includes the BBR or a predefined variation thereof. For example, the predefined variation may include a ratio or multiple of the BBR (e.g., 0×, 1×, 2×, or 3× the BBR). In some cases, methods and systems provided herein deliver insulin at the BBR regardless of a projected blood glucose level, and such a delivery approach may be referred to as a standard delivery mode.

Methods and systems provided herein can use a model to predict multiple future blood glucose levels for multiple different basal insulin delivery profiles or basal insulin delivery rates. In a feedback delivery mode, methods and systems may select one of the basal insulin delivery profiles or basal insulin delivery rates based on prediction of which profile or rate will approximate a target blood glucose level, or more specifically, select the profile that minimizes the differences between the predicted future blood glucose values and one or more target blood glucose values. In some cases, the profile that minimizes, lessons, or lowers variations from one or more target blood glucose levels in the future may be selected. The selected basal profile can then be delivered to the PWD at least until a process of evaluating different basal insulin delivery profiles or rates is repeated, or until transitioning from a feedback delivery mode to a standard delivery mode (e.g., repeated delivery of the baseline basal rate). The different basal insulin delivery profiles or rates for each evaluation process can be generated using any suitable technique or techniques.

In some cases, multiple profiles or delivery rates are generated using one or more user-specific dosage parameters. In some cases, one or more user-specific dosage parameters can be entered by a user, calculated by information entered by a user, and/or calculated by monitoring data generated from the PWD (e.g., monitoring insulin delivery rates and blood glucose data while the PWD is using a pump in an open loop mode). In some cases, methods and systems provided herein can modify user-specific dosage parameters over time based on one or more selected basal insulin delivery profiles or rates and/or other data obtained from the PWD. In some cases, the user-specific dosage parameters can be dosage parameters that are commonly used in the treatment of diabetes, such as average total daily insulin, total daily basal dose (TDBD) of insulin, average basal rate, insulin sensitivity factor (ISF), and carbohydrate-to-insulin ratio (CR). For example, in some cases, a PWD's average basal rate can be used to calculate multiple different basal insulin delivery profiles based on multiples or fractions of the average basal rate used over different intervals of time.

In some cases, methods and systems provided herein can use time-interval-specific user-specific dosage parameters (e.g., a time-interval-specific baseline basal rate). In some cases, methods and systems provided herein can make adjustments to time-interval-specific user-specific dosage parameters for each time interval for where a delivered basal rate varies from a baseline basal rate for that time interval. In some cases, user-specific dosage parameters are specific for time intervals of two hours or less, one hour or less, thirty minutes or less, or fifteen minutes or less. For example, in some cases, methods and systems provided herein can store a baseline basal rate (BBR) for the hour between 1 PM and 2 PM, and can adjust the BBR for that hour up if the method or system delivers more basal insulin during that time period and adjust the BBR down if the method or system delivers less basal insulin during that time period. In some cases, methods and systems provided herein can adjust the BBR for a time interval based on whether the method or system delivers more or less basal insulin in a subsequent time interval, which may be within 3 hours of the adjusted time interval (e.g., a method or system may adjust the BBR for the hour between 1 PM and 2 PM based on variations from BBR during the hour between 2 PM and 3 PM and/or based on variations from BBR during the hour between 3 PM and 4 PM).

In some cases, adjustments to user-specific dosage parameters can be based on a threshold variation and/or can be limited to prevent excessive adjustments to user-specific dosage parameters. For example, in some cases, a daily adjustment to a user-specific dosage parameter can be limited to less than 10%, less than 5%, less than 3%, less than 2%, or about 1%. In some cases, an adjustment to a baseline basal rate is less than a difference between the amount of basal insulin actually delivered and the baseline basal for a specific period of time (e.g., if a baseline basal rate is 1 U/hour and systems or methods provided herein actually delivered 2 U for the previous hour, the adjustment to any baseline basal rate based on that difference would be less than 1 U/hour).

Methods and systems provided herein can use any appropriate model to predict multiple future blood glucose values. In some cases, predictive models can use one or more current or recent blood glucose measurements, estimates of rates of change of blood glucose levels, an estimation of unacted carbohydrates, and/or an estimation of unacted insulin. In some cases, predictive models can use one or more user-specific dosage parameters in predicting multiple blood glucose values over a future time interval for multiple different basal insulin delivery profiles or rates over that same future time interval. That future time interval can be at least two hours, at least three hours, or at least four hours, at least five hours, etc. User-specific dosage parameters, which can be time-interval-specific, can also be used in determining an estimation of unacted carbohydrates and/or an estimation of unacted insulin. In some cases, an estimation of unacted carbohydrates and/or an estimation of unacted insulin can use a simple decay function. In some cases, an estimate of unacted insulin can be determined using an Insulin On Board (IOB) calculation, which are common in the art of treating diabetes. In some cases, an IOB calculation used in a predictive model used in methods and systems provided herein can consider insulin delivered to the PWD during the delivery of a bolus. In some cases, the IOB calculation can additionally add or subtract to the IOB based on changes to the basal insulin delivery rate from a baseline basal rate. In some cases, an estimate of unacted carbohydrates can be determined using a Carbohydrates On Board (COB) calculation, which can be based on a decay function and announced meals. In some cases, predictive models used in methods and systems provided herein can also consider the non-carbohydrate components of a meal. In some cases, methods and systems provided herein can infer an amount of carbohydrates from an unannounced meal due to a spike in up-to-date blood glucose data. In some cases, predictive models used in methods and systems provided herein can additionally consider additional health data or inputs, which may indicate that the PWD is sick, exercising, experiencing menses, or some other condition that may alter the PWD's reaction to insulin and/or carbohydrates. In some cases, at least an IOB, a COB, an insulin sensitivity factor (ISF), and a carbohydrate-to-insulin ratio (CR) are used to predict future blood glucose values for each evaluated basal insulin delivery profile or rate.

Methods and systems provided herein can set one or more blood glucose targets using any suitable technique. In some cases, a blood glucose target can be fixed, either by a user or pre-programmed into the system. In some cases, the target blood glucose level can be time interval specific (e.g., based on diurnal time segments). In some cases, a user can temporarily or permanently adjust the target blood glucose level. In some cases, methods and systems provided herein can make adjustments to target blood glucose levels in order to minimize, lessen, or lower a risk of the PWD having a hypoglycemic event. In some cases, methods and systems provided herein can make adjustments to target blood glucose levels in order to minimize, lessen, or lower a risk of the PWD having a hyperglycemic event. For example, in some cases, methods and systems provided herein can analyze a variability of blood glucose data for the PWD and select a blood glucose target based on that variability. In some cases, methods and systems provided herein can analyze the variability of blood glucose data for diurnal time segments and adjust the blood glucose target individually for each diurnal time segment. For example, some PWDs may have a lower blood glucose variability at night, thus systems and methods provided herein can reduce blood glucose targets for nighttime diurnal time segments because of the lower probability that a lower blood glucose target would result in a hypoglycemic event during those lower variability time segments. Reducing the blood glucose target for diurnal time segments having a lower variability can reduce the amount of hyperglycemic events for the PWD. In some cases, PWDs may have a larger variability around the times of day when they typically have meals (e.g., due to mismatches in timing and amounts of insulin boluses and carbohydrate ingestion), thus methods and systems provided herein can detect diurnal time segments having a wider range of variability and increase the blood glucose target for those time periods to reduce the probability of a hypoglycemic event during those time periods. In some cases, methods and systems provided herein can analyze the variability of blood glucose data for specific days of the week and/or based on other physiological patterns and adjust the blood glucose targets for that individual based on the specific day of the week or based on other physiological patterns. For example, a PWD may have certain days of the week when they exercise and/or PWD may have different insulin needs based on a menses cycle.

Methods and systems provided herein can evaluate each basal insulin delivery profile or rate to select the profile or rate that minimizes a variation from the one or more blood glucose targets using any appropriate method. In some cases, methods and systems provided herein can use a cost function to evaluate differences between the predicted blood glucose values for each basal insulin delivery profile or rate and blood glucose targets, potentially specified for a diurnal time segment. Methods and systems provided herein can then select a basal profile or rate that produces the lowest cost function value. Methods and systems provided herein can use any suitable cost function. In some cases, cost functions can sum the absolute value of the difference between each predicted blood glucose value and each blood glucose target. In some cases, cost functions used in methods and systems provided herein can use a square of the difference. In some cases, cost functions used in methods and systems provided herein can assign a higher cost to blood glucose values below the blood glucose target in order reduce the risk of a hypoglycemic event. In some cases, the cost function can include a summation of the absolute values of a plurality of predicted deviations, squared deviations, log squared deviations, or a combination thereof. In some cases, a cost function can include variables unrelated to the predicted blood glucose values. For example, a cost function can include a penalty for profiles that do not deliver 100% of the BBR, thus adding a slight preference to use 100% of BBR. In some cases, methods and systems provided herein can include a cost function that provides a slight preference to keep the existing basal modification for every other interval (e.g., a second 15-minute segment), which could reduce the variability in basal insulin delivery rates in typical situations, but allow for more critical adjustments.

Methods and systems provided herein can store a plurality of user-specific dosage parameters (e.g., BBR, CR, and ISF) as different values for a plurality of different diurnal time segments. As used herein, "diurnal time segments" periods of time during each day, such that the methods and systems will repeat use of each diurnal-specific user-specific dosage parameter during the same time on subsequent days if a stored diurnal-specific user-specific dosage parameter is not modified or changed, thus the use of the stored diurnal-specific user-specific dosage parameter will wrap each day. Methods and systems provided herein, however, can be adapted to make daily (or more or less frequent) adjustments to each diurnal-specific user-specific dosage parameter based on the operation of the system. Methods and systems provided herein may additionally store settings or adjustments for specific days of the week or for other repeating cycles.

After a basal insulin delivery profile or rate is selected, methods and systems provided herein can include the delivery of basal insulin to the PWD according to the selected basal insulin profile or rate for any suitable period of time. In some cases, methods and systems provided herein may supply basal insulin according to the selected basal insulin delivery profile or rate for a predetermined amount of time that may be less than the time interval of the evaluated basal insulin delivery profiles or rates. For example, methods and systems provided herein may analyze projected blood glucose values for basal insulin delivery profiles or rates that last over the next four hours but repeat the process of selecting a new basal insulin delivery profile or rate every fifteen minutes. In some cases, methods and systems provided herein can delay or suspend basal insulin delivery during the delivery of a bolus, which can be triggered by a user requesting a bolus.

As used herein, "basal insulin delivery" has its normal and customary meaning within the art of the treatment of diabetes. Although basal rates are expressed as a continuous supply of insulin over time, basal insulin delivery may constitute multiple discrete deliveries of insulin at regular or irregular intervals. In some cases, methods and systems provided herein may only be able to deliver insulin in discrete fractions of a unit. For example, some insulin delivery devices can only deliver insulin in a dose that are an integer multiple of 0.05 units or 0.1 units. In some cases, a delivery of basal insulin can include a delivery of insulin at predetermined time intervals less than or equal to fifteen minutes apart or less, ten minutes apart or less, or five minutes apart or less. In some cases, the time interval between discrete basal insulin deliveries can be determined based on the basal insulin delivery rate (e.g., a basal rate of 1.0 units/hour might result in the delivery of 0.1 units every six minutes). As used herein, the term "bolus" has its normal and customary meaning with the art of the treatment of diabetes, and can refer to a bolus delivered in order to counteract a meal (i.e., a meal-time bolus) and/or to correct for elevated blood glucose levels (i.e., a correction bolus). In some cases, methods, devices, and systems provided herein can automatically administer calculated doses of insulin having an upper maximum (the maximum being based on a user's nominal basal rate or other user-specific dosage parameters) based on glucose data at regular intervals of less than every 20 minutes, and such regular deliveries shall constitute a "basal insulin delivery" as the term is used herein and may be used in calculating Basal IOB in the methods and operations provided herein.

In some cases, methods and systems provided herein can determine a correction bolus based on historic blood glucose levels, a target blood glucose level, and the expected effect of personalization on projected blood glucose levels. For example, if a diabetes management system projects that a series of 2×, 2×, 2×, 2×, 1×, 1×, 1×, 1× delivery actions will bring a high blood glucose level within a threshold distance from the target blood glucose level, the system may postpone recommending a correction bolus. As another example, if the diabetes management system projects that a series of 2×, 2×, 2×, 2×, 2×, 2×, 2×, 2× delivery actions will still result in a high blood glucose level, the diabetes management system may recommend a correction bolus to the user. Additionally or alternatively, the diabetes management system may suggest a correction bolus when the PWD requests a bolus for a meal as an additional amount of insulin.

Methods and systems provided herein can trigger an alert or an alarm to be provided to the PWD or another user based on a calculated correction bolus, which may or may not be displayed or observable to a user of the methods, devices, and systems provided herein. For example, if the suggested amount of a correction bolus exceeds a threshold amount, the diabetes management system may provide an alert or alarm to the PWD, but not provide any audible or vibrational alarm or alert to the user so long as the calculated amount of a correction bolus is less than the threshold amount. In some cases, so long as the calculated amount of the correction bolus is less than the threshold, methods, systems, and devices will only provide the calculated correction bolus if the user requests a correction bolus calculation or enters a bolus calculator. In some cases, the threshold amount may be a static amount of insulin. For example, if the correction bolus exceeds three units (3 U) of insulin, the diabetes management system may provide an alert or alarm. In some cases, the threshold amount may be dynamic and may be based on a variety of factors. For example, the threshold amount may be based on a portion of the TDBD designated for a given diurnal time period or a fraction of TDBD. Additionally or alternatively, the threshold may be related to a personalized BBR for a given period of time. For example, embodiments of the present disclosure may include personalizing the BBR for a PWD for each diurnal time segment in a day independently. In these and other cases, the threshold may vary depending on the time of day as the BBR may vary depending on the time of day. For example, the threshold may be based on the sum of insulin when delivering the BBR for the next hour for the PWD, and if the correction bolus exceeds that amount of insulin, an alert may be triggered. In some cases, the threshold (e.g., based on the TDBD or the BBR) may be multiplied by a user-designated factor.

Methods and systems provided herein can in some cases include multiple delivery modes. In some cases, methods and systems provided herein can monitor the presence of blood glucose using one or more blood glucose measuring devices or methods, control or monitor the dispensation of medicine, and determine and/or update the user-specific dosage parameters regardless of the operating mode. For example, possible operating modes could include a standard delivery mode (e.g., open-loop or repeated delivery of the BBR), feedback delivery mode (e.g., closed-loop or hybrid closed-loop modes) that automatically adjust basal rates based on glucose monitoring data and other user-specific dosage parameters (e.g., baseline basal rate (BBR), insulin sensitivity factor (ISF), and carbohydrate-to-insulin ratio (CR)), modes that can use blood glucose monitor (BGM) data to update user-specific dosage parameters (e.g., BBRs, ISFs, and CRs) for different time blocks over longer periods of time, manual modes that require a patient to manually control the therapy program using an insulin pump, and advisory modes that recommend dosages for a PWD to inject using an insulin pen or syringe. By determining optimized control parameters that work across delivery modes, systems and methods provided herein can provide superior analyte control even when a PWD switches to a different delivery mode. For example, methods and systems provided herein may be forced to switch away from a hybrid closed-loop delivery mode that adjusts basal insulin delivery away from a BBR if a glucose monitor malfunctions or if the system exceeds one of the constraints.

In some cases, the constraints and/or the thresholds associated with the constraints may be modified in certain circumstances. For example, when a PWD is transitioning from manual insulin delivery treatment (e.g., using a pen/syringe to deliver long-acting insulin) to utilize a feedback delivery mode system (e.g., using a pump and CGM to deliver insulin in an automated way), the constraints may be modified. In these and other embodiments, it may be determined when a PWD received their last dose of long-acting insulin. Based on when the long-acting insulin was last delivered, the system may limit the amount of insulin delivered based on the typical personalization algorithm. For example, if the delivery actions include 1×, 1×, 1×, 2×, 2×, 2×, 2×, 2×, the system may constrain the delivery to a reduced amount of insulin, such as 25% of the planned delivery. In some cases, methods, systems, and devices can deliver basal insulin according to a feedback delivery mode during a certain period of time after the delivery of long-acting insulin (e.g., 24 hours), but only deliver a reduced percentage (e.g., 25%) of BBR when the system enters an open-looped mode during that certain period of time in order to ensure that the PWD does not receive excessive insulin when glucose data is not being used to modulate basal insulin deliveries. Additionally or alternatively, the delivery actions may permit no insulin delivery until a certain period of time (e.g., 24 hours) after the last delivery of long-acting insulin. For example, if the past delivery actions include a series of 0× delivery actions beyond a threshold, the system may normally transition to the standard delivery mode to deliver the BBR. However, if the PWD has had a dose of long-acting insulin within a certain period of time (e.g., 24 hours), the system may permit a series of 0× deliveries beyond the threshold without transitioning to the standard delivery mode. In some cases, such as a standard delivery mode (e.g., delivering the BBR), the system may constrain delivery to a reduced amount of insulin for a period after the last long-acting insulin dose. For example, the system may constrain delivery of insulin to 25% of the BBR for the first 24 hours after the last dose of long-acting insulin.

FIG. 1 provides an example diabetes management system 10, in accordance with one or more embodiments of the present disclosure. The system 10 may include a pump assembly 15 for providing insulin and a glucose monitor 50. As shown, the glucose monitor 50 is in wireless communication with pump assembly 15. In some cases, a glucose monitor can be in wired communication with pump assembly 15. In some cases not shown, a glucose monitor can be incorporated into an insulin pump assembly. As shown, pump assembly 15 can include a reusable pump controller 200 that forms part of the pump assembly 15. In some cases, reusable pump controller 200 is adapted to determine one or more basal delivery rates. In some cases, the glucose monitor 50 can act as a controller adapted to communicate basal delivery rates to pump assembly 15.

Pump assembly 15, as shown, can include reusable pump controller 200 and a disposable pump 100, which can contain a reservoir for retaining insulin. A drive system for pushing insulin out of the reservoir can be included in either the disposable pump 100 or the reusable pump controller 200 in a controller housing 210. Reusable pump controller 200 can include a wireless communication device 247, which can be adapted to communicate with a wireless communication device 54 of glucose monitor 50 and other diabetes devices in the system 10, such as those discussed below. In some cases, pump assembly 15 can be sized to fit within a palm of a hand 5. Pump assembly 15 can include an infusion set 146. Infusion set 146 can include a flexible tube 147 that extends from the disposable pump 100 to a subcutaneous cannula 149 that may be retained by a skin adhesive patch (not shown) that secures the subcutaneous cannula 149 to the infusion site. The skin adhesive patch can retain the cannula 149 in fluid communication with the tissue or vasculature of the PWD so that the medicine dispensed through tube 147 passes through the cannula 149 and into the PWD's body. Cap device 130 can provide fluid communication between an output end of an insulin cartridge (not shown) and tube 147 of infusion set 146. Although pump assembly 15 is depicted as a two-part insulin pump, one piece insulin pumps are also contemplated. Additionally, insulin pump assemblies used in methods and systems provided herein can alternatively be a patch pump.

In some cases, controller 200 can include a user interface. In some cases, the primary user interface can be present on a remote display device 60. In some cases, as shown, controller 200 can include a button 220 and a plurality of illuminable icons 221-225, which can be used to provide information about the operation of the system 10 when the display device 60 is out of communication with the controller 200. In some cases, button 220 can be pressed by a user to ask the system to illuminate the icons 221-225 as appropriate in order to determine the operation of the system. In some cases, a user can press button 220 in order to acknowledge alerts or alarms. In some cases, a user can long press and/or press button 220 in predetermined patterns in order to provide confirmation of delivery instructions from the display device 60. In some cases, methods and systems provided herein can have display device 60 provide instructions to a user to interact with one or more buttons on controller 200 if a bolus instruction being sent to the controller 200 exceeds a bolus threshold, which may be based on a bolus amount, a time since the last bolus, a current IOB, and/or a projected IOB after the delivery of the bolus.

The glucose monitor 50 can include a housing, a wireless communication device 54, and a sensor shaft. The wireless communication device 54 can be contained within the housing and the sensor shaft can extend outward from the housing. In use, the sensor shaft can penetrate the skin 20 of a user to make measurements indicative of the PWD's blood glucose level or the like. In some cases, the sensor shaft can measure glucose or another analyte in interstitial fluid or in another fluid and correlate that to blood glucose levels.

In some cases, the glucose monitor 50 may include a flash glucose monitor (FM) such that the glucose monitor 50 may invoke the sensor shaft and obtain a reading of the blood glucose levels based on the PWD invoking the glucose monitor 50. Additionally or alternatively, the glucose monitor 50 may periodically store blood glucose readings and may provide those stored readings when the glucose monitor 50 is invoked by the PWD. For example, the PWD may swipe, move or otherwise bring one or more devices of the diabetes management system 10 in physical proximity to the glucose monitor 50. In some cases, the devices may include a near-field communication (NFC) device to facilitate invocation of the glucose monitor 50. For example, the pump assembly 15 may include an NFC device 248, a display device 60 may include an NFC device 65, and a bolus administering device 80 may include an NFC device 85. In response to the invocation of the glucose monitor 50, the glucose monitor 50 can employ the wireless communication device 54 to transmit data to a corresponding wireless communication device 247 housed in the pump assembly 15. In some cases, the glucose monitor 50 may include a circuit that permits sensor signals (e.g., data from the sensor shaft) to be communicated to the wireless communication device 54. The wireless communication device 54 can transfer the collected data to reusable pump controller 200 (e.g., by wireless communication to the wireless communication device 247).

Diabetes management system 10 may optionally include a blood glucose meter 70 (e.g., a glucose sensor). In some cases, blood glucose meter 70 can be in wireless communication with reusable pump controller 200. Blood glucose meter 70 can take a blood glucose measurement using one or more test strips (e.g., blood test strips). A test strip can be inserted into a strip reader portion of the blood glucose meter 70 and then receive the PWD's blood to determine a blood glucose level for the PWD. In some cases, the blood glucose meter 70 is configured to analyze the characteristics of the PWD's blood and communicate (e.g., via a BLUETOOTH® wireless communication connection, an NFC connection, etc.) the information to reusable pump controller 200. In some cases, a user can manually input a glucose meter reading. The blood glucose meter 70 can be manually operated by a user and may include an output subsystem (e.g., display, speaker) that can provide the user with blood glucose readings that can be subsequently entered into the controller or user interface to collect the data from an unconnected BGM into the system. The blood glucose meter 70 may be configured to communicate data (e.g., blood glucose readings) obtained to reusable pump controller 200 and/or other devices, such as the display device 60. Such communication can be over a wired and/or wireless connection, and the data can be used by system 10 for a number of functions (e.g., calibrating the glucose monitor 50, confirming a reading from the glucose monitor 50, determining a more accurate blood glucose reading for a bolus calculation, detecting a blood glucose level when the glucose monitor 50 is malfunctioning, etc.).

In some cases, the system 10 can further include a control device that can communicate with the reusable pump controller 200 through a wireless and/or wired connection with the reusable pump controller 200 (e.g., via a BLUETOOTH® wireless communication connection or a near-field communication connection). In some cases, the control device communicates wirelessly with other diabetes devices of system 10. The control device can be any of a variety of appropriate computing devices, such as a smartphone, a tablet computing device, a wearable computing device, a smartwatch, a fitness tracker, a laptop computer, a desktop computer, a smart insulin pen (e.g., bolus administering device 80), the pump controller 200, and/or other appropriate computing devices. In some cases (for example, where the reusable pump controller 200 does not determine a basal delivery rate), the control device can receive and log data from other elements of the system 10 and determine basal delivery rates using any method or approach, such as those described in U.S. patent application Ser. No. 15/601,282, the disclosure of which is hereby incorporated herein in its entirety by this reference. In some cases, the basal delivery rate may be based at least in part on projected blood glucose levels. For example, the control device may predict future blood glucose levels based on historical readings, current IOB, expected delivery rate, etc. The control device may project and/or predict future blood glucose levels in any predictive manner, such as those described in U.S. patent application Ser. No. 15/601,282.

In some cases, the control device can personalize delivery of insulin to the PWD. For convenience, such personalization will be described as a series of delivery actions of 0×, 1×, or 2× of a baseline basal rate (BBR) based on attempting to achieve a target blood glucose level. However, any personalization algorithm and predetermined variations on the BBR are within the scope of the present disclosure. For example, the personalization algorithm may include 0×, 0.5×, 0.75×, 1×, 1.25×, 1.5×, 2×, 2.5×, 3×, etc. In some cases, the control device may generate multiple series of delivery actions and select the set of delivery actions that most closely approaches the target blood glucose level.

In some cases, the control device can adjust the selected set of delivery actions and/or transition the system 10 out of a feedback delivery mode (e.g., where the delivery actions may include 0×, 1×, or 2× the BBR) and into a standard delivery mode (e.g., where the delivery actions include 1× the BBR). Such adjustments may be based on previous delivery actions of insulin. For example, in some cases, the control device can monitor the personalized delivery actions relative to a threshold. Such a threshold may be based on a duration of time that a particular delivery action has been occurring, the amount of insulin delivered based on the delivery actions, etc.

With respect to constraints related to excessive insulin delivery, the threshold may be based on a number of actions, an elapsed amount of time, an amount of insulin delivered, etc., or combinations thereof. For example, the control device may monitor the amount of basal insulin delivered and if the amount of basal insulin delivered exceeds a percentage of the total daily basal dose (TDBD) for the PWD over a set period of time, the control device may transition the system 10 out of the feedback delivery mode and into the standard delivery mode for a certain amount of time. The threshold may also be based off of a percentage of the TDBD over a period of time, e.g., 10%, 12%, 14%, 16%, etc., of the TDBD over 2 hours, 3 hours, 4 hours, or 5 hours. In these and other embodiments, the threshold may be based off a duration of time that the system provides 2× the BBR (e.g., the last four hours, the last three hours, etc.). In response, the control device may transition the system out of the feedback delivery mode and into the standard delivery mode, which may be represented to a user on the display device 60 and/or by a change to an icon 221 on controller 200. In some cases, the transition to the standard delivery mode can be accompanied by an alert. In some cases, methods, devices, and systems provided herein may require the user to obtain a blood glucose measurement from a finger stick (e.g., from BGM 70) in order to return to a feedback mode. In some cases, the alarm or alert can indicate that the user should consider a correction dose of insulin after the user obtains or enters a blood glucose measurement. Pushing the system out of feedback mode unless a user enters a blood glucose value from a finger stick can, in some cases when the system is a hybrid closed-loop system requiring user initiated boluses for meals, provide reinforcement for a user to routinely bolus for meals rather than merely having the modulation of basal rates attempt to overcome high blood glucose levels caused by eating without taking a bolus of insulin to account for the meal. In some cases, the monitoring for excessive insulin delivery may or may not exclude bolus insulin when determining whether or not to transition to the standard delivery mode. For example, in some cases, the monitoring for excessive insulin deliveries can only consider whether a Basal IOB is above a threshold, excluding consideration of a Bolus IOB.

With respect to constraints related to insufficient insulin delivery, the threshold may be based on a number of actions, an elapsed amount of time, an amount of insulin delivered, etc., or combinations thereof. For example, the control device may monitor the amount of insulin delivered to the PWD and compare it to the insulin for the PWD at their normal BBR. Such monitoring may be based on the normal baseline basal insulin delivered, any bolus insulin delivered, and any adjustments to the baseline basal insulin. In these and other cases, that amount of insulin may be compared to a threshold amount, for example, 60%, 50%, 40%, etc., of the normal baseline basal insulin. In these and other embodiments, the comparison may be based on IOB rather than insulin delivered. Such an analysis may account for variations in the user-specific dosage parameters (e.g., ISF and CR). Stated mathematically:

$$\text{Total } IOB \text{ Ratio} = \frac{\text{Total } IOB_t}{\text{Nominal Basal } IOB_t} =$$

$$\frac{\text{Nominal Basal } IOB_t + \text{Bolus } IOB_t + \text{Basal Adjust } IOB_t}{\text{Nominal Basal } IOB_t}$$

where Total $IOB_t$ represents the total active insulin the body of the PWD at a time t, Nominal Basal $IOB_t$ represents the IOB at time t that would be present for a PWD if the PWD only received the PWD's BBR, Bolus $IOB_t$ represents the IOB at time t based on any boluses delivered to the PWD, and Basal Adjust $IOB_t$ represents the IOB at time t based on any delivery actions outside of the BBR (e.g., 0× or 2× the BBR), with deliveries at 0× counting negatively and at 2× counting positively. Thus, the Total IOB Ratio calculated may represent a ratio of the total IOB and the IOB that would be present if the PWD were only receiving their standard BBR. This ratio may be compared to a threshold, such as 0.75, 0.6, 0.55, 0.5, 0.45, 0.4, 0.25, etc. If the Total IOB Ratio falls below the threshold, it can indicate that the PWD is not receiving a sufficient amount of insulin to account for the PWD's basic insulin needs, thus methods, devices, and systems provided herein can override a feedback delivery mode's determination to administer less than BBR if the Total IOB Ratio falls below a threshold.

Additionally, a calculation of a Total IOB Ratio, Total IOB, or just a Bolus IOB can be used to determine whether to require a user to take additional steps to confirm the user's intent to deliver a bolus of insulin. For example, if a user has a Total IOB or Bolus IOB of greater than 25%, 30%, 35%, 40%, 45%, or 50% of the user's TDBD, methods, devices, and systems provided herein can require that a bolus instruction being sent to the controller 200 via display device 60 be confirmed by the user by pressing button 220 or by pressing button 220 for a certain length of time or using a certain press pattern. In some cases, a requirement to press a button on a pump assembly may be based on a time difference between the current bolus instruction and the prior bolus instructions (e.g., if the bolus instructions are within 1 hour).

With respect to constraints related to excessive basal insulin delivery, the threshold may be based on a Basal IOB Ratio, stated mathematically as:

$$\text{Basal } IOB \text{ Ratio} = \frac{\text{Nominal Basal } IOB_t + \text{Basal Adjust } IOB_t}{\text{Nominal Basal } IOB_t}$$

Thus, the Basal IOB Ratio calculated may represent a ratio of the IOB due only to actual basal delivery actions to the IOB that would be present if the PWD were only receiving their standard BBR. This ratio may be compared to an upper threshold, such as 1.90, 1.85, 1.80, 1.75, or 1.70, etc. If the Basal IOB Ratio is above the threshold, it can indicate that the PWD ate without delivering a bolus or that a glucose sensor is malfunctioning. Thus, methods, devices, and systems provided herein can override a feedback delivery mode's determination to deliver insulin in amounts greater than BBR if the Basal IOB Ratio exceeds a threshold, and in some cases, as discussed above, potentially exit the feedback delivery mode to require the user to enter additional data or take additional actions before entering the feedback mode again.

In some cases, the control device may utilize constraints related to both delivery of an excessive amount of insulin and related to delivery of an insufficient amount of insulin.

In some cases, a PWD may be transitioning from utilizing a daily/periodic insulin injection device (e.g., a pen) for receiving their basal insulin (e.g., utilizing a long-acting insulin device (not shown)) to a device such as the system 10 that may continuously or in an automated fashion deliver insulin via a pump or other similar or comparable device. In these and other cases, the period of transition from the long-acting insulin to the pump or other similar device may or may not include variations to the constraints described above. For example, when a PWD first begins using an insulin pump and has long-acting insulin in their system, the personalization may select a series of delivery actions including 0×, 0×, 0×, 0×, 0×, 0×, 0×, 0×. Under typical constraints, if such a series of delivery actions was continued, the system may transition from the feedback delivery mode to the standard delivery mode and delivery 1× the BBR. However, as the PWD still has long-acting insulin in their body, the system 10 may allow the personalization to continue to deliver 0× the BBR for a transition period after their last dose of long-acting insulin. For example, the PWD (or another user, e.g., a doctor) may input the last time the PWD received a dose of long-acting insulin and the system 10 may allow the personalization to deliver 0× for 12 hours, 18 hours, 24 hours, 36 hours, etc., or another value based on the response curve of the insulin used. As another example, if the PWD is not using a feedback delivery mode but is using a standard delivery mode (e.g., delivering the BBR of basal insulin), the system 10 may not deliver the full BBR for a transition period after the last dose of long-acting insulin. For example, the system 10 may deliver 20%, 25%, 33%, 50%, etc. of the BBR for 12 hours, 18 hours, 24 hours, 36 hours, etc., or another value based on the response curve of the insulin used.

In some cases, when one of the constraints is triggered, an alarm may be sent to the PWD or another user (e.g., a doctor or caregiver) indicating that the constraint was triggered. In these and other cases, a setting may be included for the system 10 to suppress or otherwise prevent or delay presentation of alarms. For example, if the constraint is triggered during the middle of the night, the system 10 may delay sending the alarm until after 6 AM. In some cases, after acknowledging the alarm, the user may be able to transition the system 10 back into a feedback delivery mode. In some cases, there may be a lockout period such that if the user transitions back into the feedback delivery mode a certain number of times within the lockout period, the system 10 may prevent the user from putting the system back into the feedback delivery mode.

In some cases, a user can input relevant data into the control device. For example, the user may input the time of the last dose of long-acting insulin for the PWD. In some cases, the control device can be used to transfer data from the reusable pump controller 200 to another computing device (e.g., a back-end server or cloud-based device).

In some cases, the display device 60 provides a user interface (e.g., graphical user interface (GUI), speech-based user interface, motion-controlled user interface) through which users can provide information to control operation of the control device, the reusable pump controller 200, and/or other devices in the system 10. For example, the display device 60 can be a mobile computing device running a mobile app that communicates with reusable pump controller 200 over short-range wireless connections (e.g., BLUETOOTH® connection, Wi-Fi Direct connection, near-field communication (NFC) connection, etc.) to provide status information for the system 10 and allow a user to control operation of the system 10 (e.g., toggle between delivery modes, adjust settings, log food intake, confirm/modify/cancel bolus dosages, and the like).

The system 10 may include a bolus administering device 80 (e.g., a syringe, an insulin pen, a smart syringe with device communication capabilities, or the like) through which bolus doses can be manually administered to a PWD. In some cases, a suggested dosage for a bolus to be administered using the bolus administering device 80 can be output to a user via the user interface of reusable pump controller 200 and/or the user interface of the display device 60. In some cases, the bolus administering device 80 can communicate through a wired and/or wireless connection with reusable pump controller 200 and/or the display device 60. In some cases, the system 10 can allow users to input insulin deliveries made using a syringe or insulin pen.

Bolus Alarms

In some cases, the system 10 may be configured to generate an alert or alarm based on one or more factors associated with a bolus. For example, if a correction bolus is determined to be above a threshold, the system 10 may generate an alert or an alarm to the PWD. A correction bolus may include a delivery of insulin with the purpose of offsetting a high blood glucose level rather than to address an intake in carbohydrates, such as from a meal. In some cases, a correction bolus may be provided to a PWD simultaneously with a meal bolus (e.g., the meal bolus may be increased by a certain amount to account for the high blood glucose level). In some cases, a correction bolus may be based on an estimated blood glucose level (EGV) (e.g., the estimated current or a projected blood glucose level), a target blood glucose level (Target) (e.g., the desired blood glucose level for the PWD), the ISF, and the IOB of the PWD. For example, the correction bolus may be determined based on the equation:

$$\frac{EGV - \text{Target}}{ISF} - IOB$$

As used in conjunction with alarms associated with one or more correction boluses, the IOB may include any variation on IOB consistent with the present disclosure, including Total $IOB_t$, Nominal Basal $IOB_t$, Bolus $IOB_t$, and/or Basal Adjust $IOB_t$, where Total $IOB_t$ represents the total active insulin in the body of the PWD at a time t, Nominal Basal $IOB_t$ represents the IOB at time t based on the normal BBR, Bolus $IOB_t$ represents the IOB at time t based on any boluses delivered to the PWD, and Basal Adjust $IOB_t$ represents the IOB at time t based on any delivery actions outside of the BBR (e.g., 0× or 2× the BBR).

In some cases, the correction bolus amount of insulin may be compared to a threshold. In some cases, the threshold may be a static amount of insulin. For example, the amount of insulin may include a certain number of units of insulin that may be set by a caregiver or the PWD. In some cases, the threshold may be based on a dynamic value that may change based on the personalization of insulin treatment in accordance with the present disclosure. For example, in personalizing the baseline basal rate for the PWD over time, the basal rate for various diurnal time blocks throughout the day may change, and the total daily basal dose (TDBD) for the PWD may change.

In some cases, the threshold may be based on variations in the baseline basal rate for various diurnal time blocks. For example, the diabetes management system 10 may suggest a correction bolus to the PWD. In making such a suggestion, the system 10 may determine the BBR for the diurnal time blocks covering the next hour or next two hours and may compare the correction bolus to the accumulation of baseline basal insulin for the next hour or next two hours. If the correction bolus is above the accumulation of the baseline basal insulin, the system 10 may generate an alert to the PWD. The time window looking forward may be any length of time, e.g., thirty minutes, one hour, two hours, four hours, etc. Stated mathematically, the determination of whether to trigger an alert or alarm may be described as:

$$\frac{EGV - \text{Target}}{ISF} - IOB \geq \sum_{t} BBR$$

where t includes the period of time over which the baseline basal insulin is accumulated.

In some cases, the threshold may be based on a certain portion of the TDBD, or the portion of the TDBD attributable to a certain period of time. For example, the TDBD may be divided into twenty four portions corresponding to one full day and the correction bolus may be compared to the amount of insulin for one hour's worth of the TDBD. In these and other embodiments, by dividing the TDBD into portions of the day, variations in the BBR for the various portions of the day may be normalized such that a more consistent threshold may be used. Stated mathematically, the determination of whether to trigger an alert or alarm based on such a threshold may be described as:

$$\frac{EGV - \text{Target}}{ISF} - IOB \geq \frac{TDBD}{p}$$

where p includes the number of periods in a day over which the TDBD is being divided. For example, if each hour were being accounted for, p is 24; as another example, if two hours were being accounted for, p is 12.

In some cases, the determination of whether or not to trigger an alert or an alarm may include a factor applied to the threshold. For example, a user may desire that an alert may trigger more readily when a correction bolus is high, or may desire a higher correction bolus before an alert is triggered. In these and other cases, a multiplicative factor (e.g., 0.5, 1, 2, 3, 4, 5, etc.) may be applied to the threshold when making the determination of whether to trigger an alert or an alarm. Stated mathematically for both thresholds described above:

$$\frac{EGV - \text{Target}}{ISF} - IOB \geq f * \sum_{t} BBR$$

$$\frac{EGV - \text{Target}}{ISF} - IOB \geq f * \frac{TDBD}{p}$$

where f represents the multiplicative factor. In some cases, the factor (f) may be set by the PWD or a caregiver. Additionally or alternatively, the alert or alarm may be stored in a log that may be periodically provided to the PWD, a caregiver, or a medical device developer. Such a log may facilitate improvements in treatment of the PWD as the frequency and relationship of the correction bolus to the basal rate may be observed.

While one embodiment of a diabetes management system is illustrated in FIG. 1, it will be appreciated that any number, type, or style of diabetes management devices may be utilized in conjunction with the present disclosure. For example, a patch pump, a syringe, etc., may be utilized to enter doses of insulin delivered to a PWD.

Modifications, additions, or omissions may be made to FIG. 1 without departing from the scope of the present disclosure. For example, the system 10 may include any type or style of insulin delivery devices and/or monitoring devices. As another example, the display device 60 may take any form or style of computing device. As an additional example, the display device 60 may be coupled with a remote cloud device (not illustrated) that may store one or more aspects of the monitored and/or projected blood glucose levels and/or insulin delivery rates and/or projections. Such a cloud device may be accessible by a third party (e.g., a physician) or a PWD.

Figure 2A:
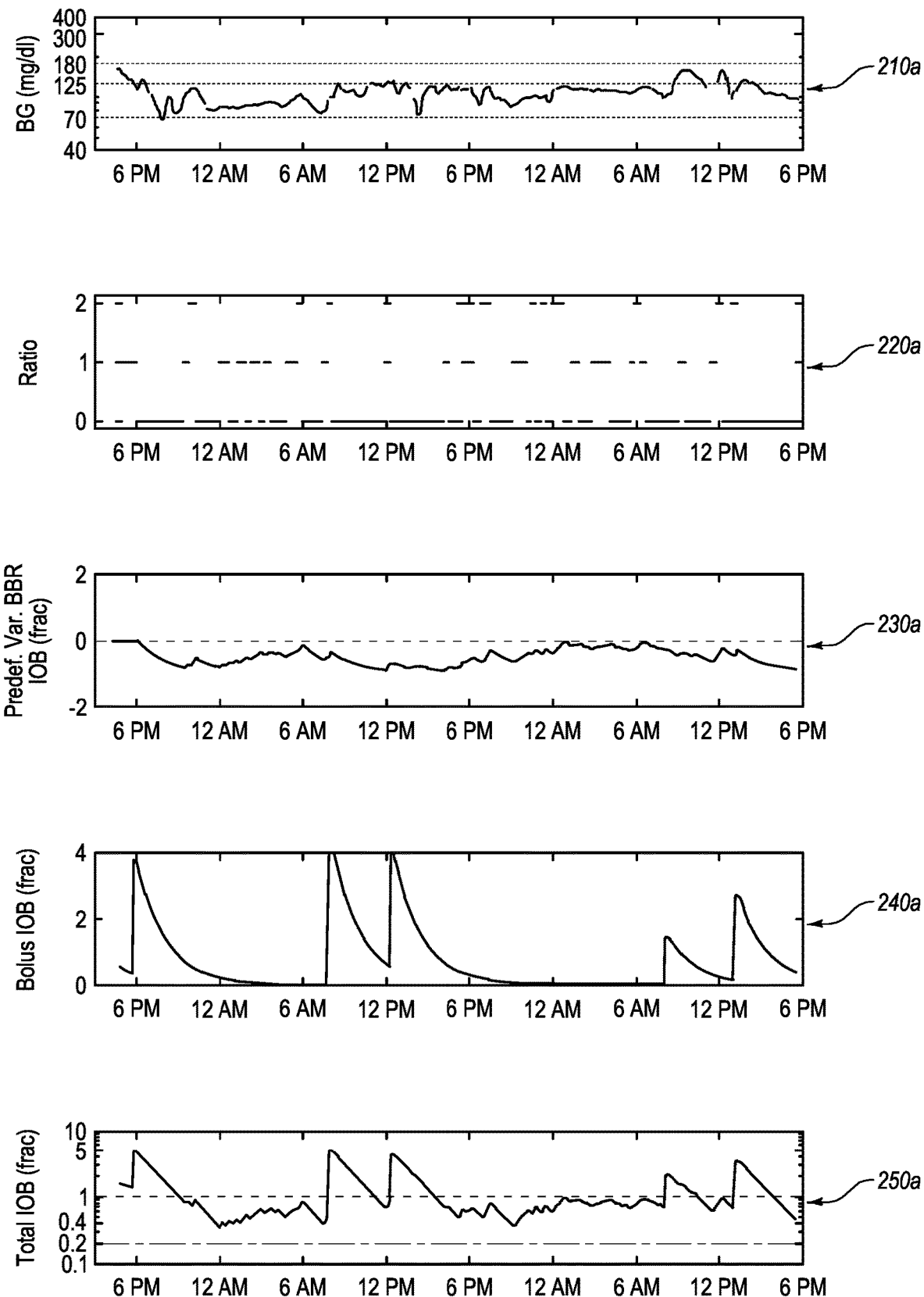
FIGS. 2A and 2B each illustrate a series of example graphs illustrating personalization of insulin delivery.
Figure 2B:
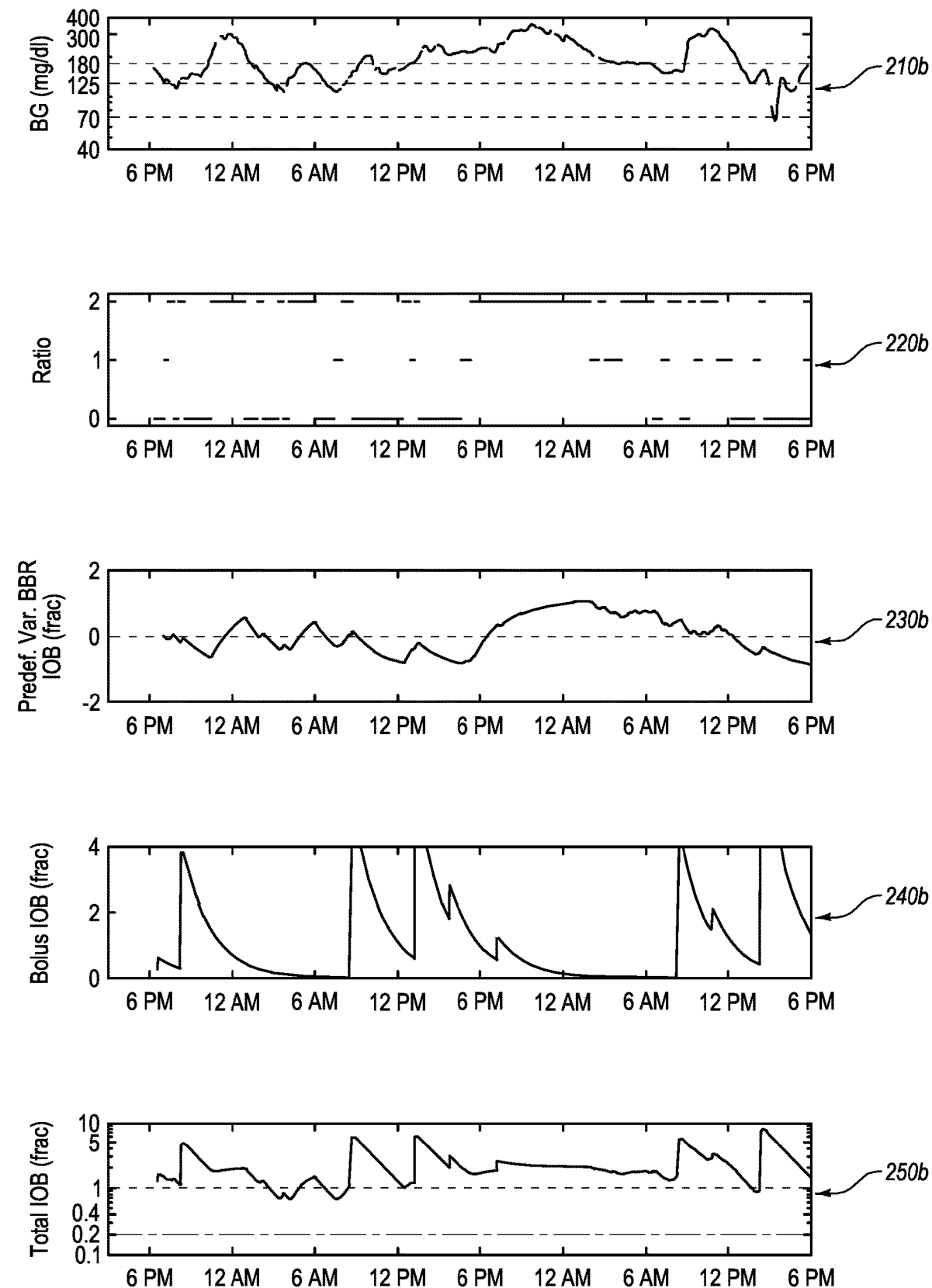

FIGS. 2A and 2B each illustrate a series of example graphs illustrating personalization of insulin delivery, in accordance with one or more embodiments of the present disclosure. FIGS. 2A and 2B include a graphs that represent blood glucose levels (BG in mg/dl) for a PWD (graphs 210*a* and 210*b*), graphs that represent the ratio of BBR delivered (0×, 1×, 2×) for various delivery actions (graphs 220*a* and 220*b*), graphs that represent what fraction of IOB is due to predefined variations in BBR relative to IOB based on the BBR (graphs 230*a* and 230*b*), graphs that represent what fraction of IOB is due to bolus insulin relative to IOB based on the BBR (graphs 240*a* and 240*b*), and graphs that represent the total IOB as a multiple of the IOB that would be present with delivery of just the BBR of insulin (graphs 250*a* and 250*b*).

With reference to FIG. 2A, the graph 210*a* shows that the BG of the PWD remains relatively level, remaining consistently between 180 mg/dl and 70 mg/dl. However, when observing the graph 220*a*, it can be observed that there are long stretches during the day in which the user receives 0× the BBR. As the delivery actions are 0×, the ratio of IOB due to predefined variations to the BBR drop below zero, as shown in the graph 230*a*. Additionally, the PWD received large boluses around breakfast time and lunch time, but did not bolus around dinner time as illustrated by the two spikes at 7 or 8 AM and 12 PM on the graph 240*a*. As the boluses occur, much of the total IOB is due to the bolus insulin, as seen in the graph 250*a*.

The graph 250*a* may illustrate certain times at which a minimum insulin delivery constraint may be invoked. For example, if the threshold were the Total IOB Ratio being at least 0.5 at approximately 12 AM, the total IOB drops to approximately 0.4 of the IOB and would invoke the constraint. At that point, a control device may transition out of a feedback delivery mode to a standard delivery mode (or temporarily override the feedback delivery mode determination to deliver less than BBR) such that 1× of the BBR may be delivered until the ratio of total IOB to IOB due to BBR is above 0.5. The constraint may also be triggered at approximately 9 PM.

In some cases, triggering the constraint may cause an alarm to be presented to the PWD. If the PWD has elected to suppress alarms during the night, the constraint at 12 AM may not be presented to the PWD until 6 AM and the system may remain in a standard delivery mode (e.g., delivering 1× the BBR) until the morning when the PWD may acknowledge the alarm (not illustrated in the graphs of FIG. 2A).

With reference to FIG. 2B, the graph 210*b* shows that the BG of the PWD goes relatively high when compared to the BG of FIG. 2A. Additionally, when observing the graph 220*b*, it can be observed that there is a long stretch from just before 6 PM to approximately 2 AM in which the user repeatedly receives 2× the BBR. As the delivery actions are 2×, the ratio of IOB due to predefined variations of the BBR continues to climb higher above zero, as shown in the graph 230b. As the system continues to deliver 2× for an extended period of time, at some point, the Basal IOB Ratio may approach a value of 2. For example, at approximately 10 PM, the amount of basal insulin delivered may exceed the 1.85 threshold (which would be about 17% of TDBD) as illustrated in the graph 230b. Based on the constraint being triggered, the system may transition into a standard delivery mode and may deliver 1× the BBR in order to reduce the Basal IOB Ratio over time.

In some cases, the system may provide an alarm to the user based on the constraint being triggered. For example, the alarm may indicate that excess basal insulin may have been delivered and the system is transitioning to a standard delivery mode. The user may acknowledge the alarm and transition the system back into the feedback delivery mode. In some cases, the system may defer or postpone delivering the alarm. For example, the PWD may desire to have the system remain in the standard delivery mode during the night and be notified in the morning, at which point the PWD may transition the system back into the feedback delivery mode.

Figure 3A:
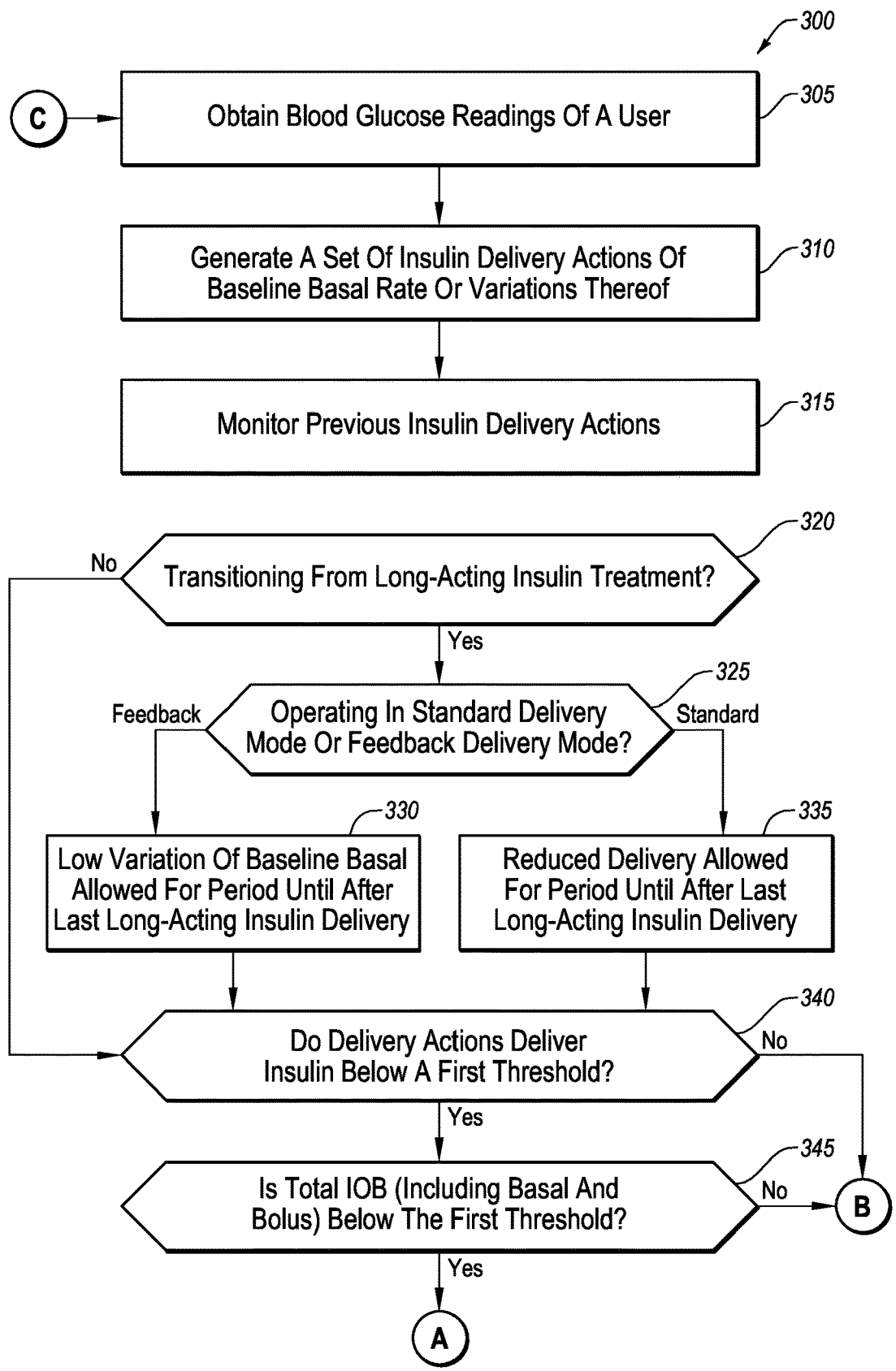
FIGS. 3A and 3B illustrate a flowchart of an example method of providing insulin delivery subject to constraints.
Figure 3B:
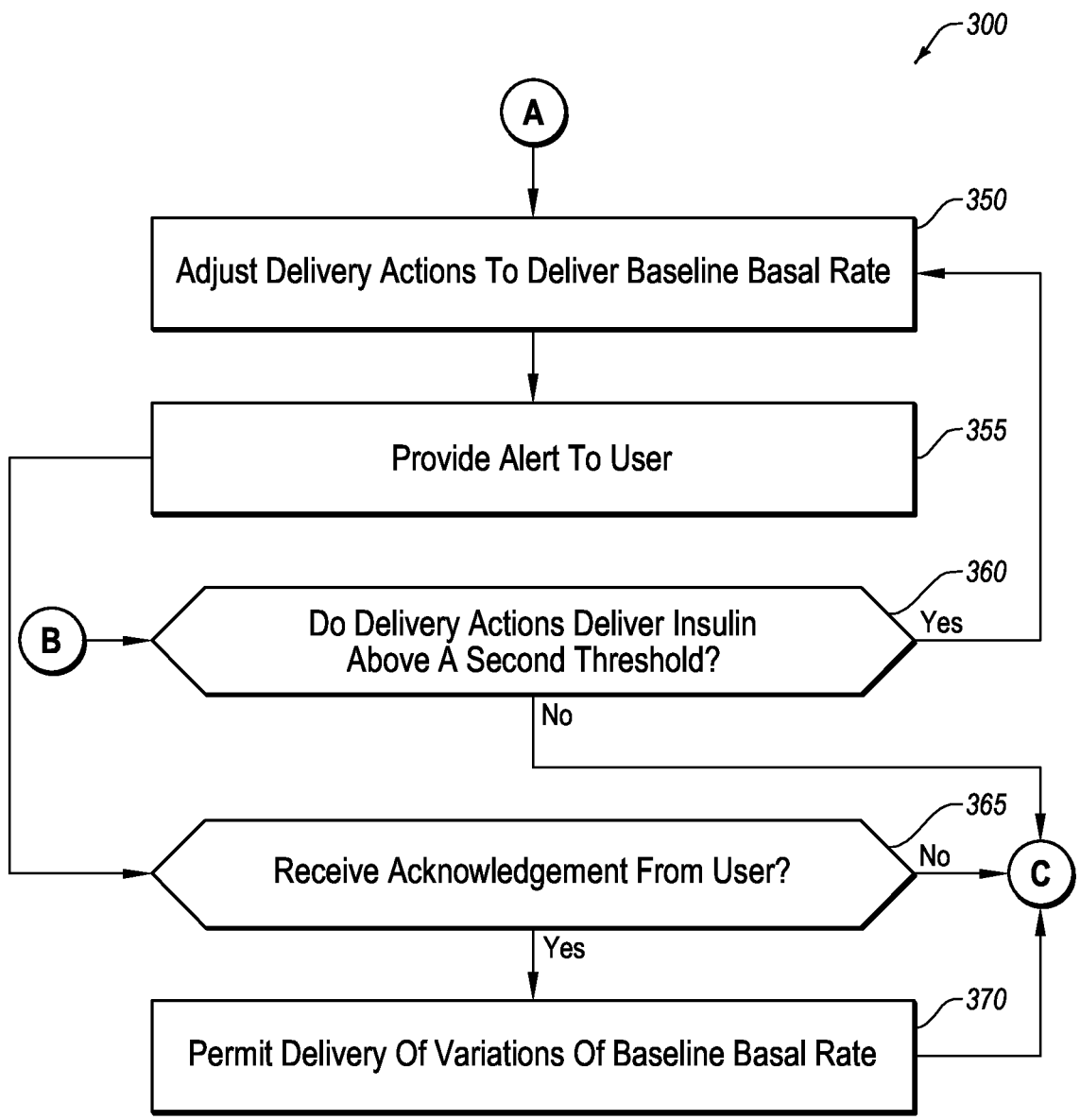

FIGS. 3A and 3B illustrate a flow diagram of an example method 300 of providing insulin delivery subject to constraints, in accordance with one or more embodiments of the present disclosure. The method 300 may be performed by any suitable system, apparatus, or device. For example, the system 10, the pump assembly 15, the control device of FIG. 1, and/or a remote server may perform one or more of the operations associated with the method 300. Although illustrated with discrete blocks, the steps and operations associated with one or more of the blocks of the method 300 may be divided into additional blocks, combined into fewer blocks, or eliminated, depending on the desired implementation.

At block 305, blood glucose readings may be obtained for a user. For example, a CGM, FM, or BGM, or other glucose monitoring device may measure and/or sense blood glucose readings for the user. For example, a control device may query a CGM and/or the CGM may automatically communicate the blood glucose readings to the control device.

At block 310, a set of delivery actions may be generated based on the blood glucose readings obtained at the block 305. For example, the control device may generate one or more sets of delivery actions to be selected and utilized. The set of delivery actions may include one or more actions of delivering insulin at the baseline basal rate (BBR) of the user or a predefined variation of the BBR. For example, the set of delivery actions may include 0×, 1×, 2×, or 3× the BBR of the user. In some cases, the set of delivery actions may be personalized and/or selected based on the feedback of the blood glucose readings. In these and other cases, the set of delivery actions may be produced in a feedback insulin delivery mode (e.g., able to deliver the BBR or predefined variations of the BBR) or a standard delivery mode (e.g., able to deliver the BBR).

At block 315, previous delivery actions may be monitored. For example, the control device may monitor which delivery actions have occurred to deliver insulin to the user. In some cases, the previous delivery actions may be stored for reference.

At block 320, a determination may be made whether or not the user is transitioning from long-acting insulin treatment. For example, if a PWD has previously treated their diabetes with a pen or other device to deliver long-acting insulin for their basal insulin, and is transitioning to a more automated system such as the diabetes management system 10 of FIG. 1, certain aspects of the constraints of the present disclosure may be modified or adjusted. For example, the constraint related to an insufficient amount of insulin or the constraint related to excessive insulin may be modified or adjusted. If it is determined that the user is transitioning from long-acting insulin delivery treatment, the method 300 may proceed to the block 325. If it is determined that the user is not transitioning from long-acting insulin treatment, the method 300 may proceed to the block 340.

At block 325, a determination may be made whether the delivery system is operating in a standard delivery mode (e.g., delivering the BBR) or a feedback delivery mode (e.g., delivering any of 0×, 1×, or 2×, or some other predetermined variation of the BBR based on a personalized set of delivery actions attempting to achieve a target blood glucose level). If it is determined that the delivery system is operating in the feedback delivery mode, the method 300 may proceed to the block 330. If it is determined that the delivery system is operating in the standard delivery mode, the method 300 may proceed to the block 335.

At block 330, when in feedback delivery mode, a low predetermined variation of the BBR may be permitted for delivery for a certain period of time after the last long-acting insulin delivery. For example, the system may allow repeated delivery of 0× the BBR for up to 24 hours after the last dose of long-acting insulin.

At block 335, when in standard delivery mode, a reduced insulin delivery may be allowed for a certain period of time after the last long-acting insulin delivery. For example, the system may utilize delivery actions of 25% of the BBR for 24 hours after the last dose of long-acting insulin.

At block 340, a determination may be made whether the delivery actions deliver insulin below a first threshold. For example, the monitored insulin delivery actions of the block 315 may be monitored to determine whether an insufficient amount of insulin is being provided to the user. In some cases, the determination may include determining how long the delivery system has been delivering 0× or some other predefined variation of the BBR below 1× the BBR. If the delivery actions are delivering insulin below the first threshold (e.g., if the constraint is triggered), the method 300 may proceed to the block 345. If the delivery actions are not delivering insulin below the first threshold, the method 300 may proceed to the block 360.

At block 345, a determination may be made whether the Total IOB Ratio (e.g., including both basal insulin and bolus insulin) is below the first threshold. In some cases, the determination may include a comparison of the Total IOB Ratio to the amount of IOB that would be present if delivering the BBR. For example, the Total IOB Ratio may be determined based on:

$$\text{Total IOB Ratio} = \frac{\text{Total } IOB_t}{\text{Nominal Basal } IOB_t} =$$

$$\frac{\text{Nominal Basal } IOB_t + \text{Bolus } IOB_t + \text{Basal Adjust } IOB_t}{\text{Nominal Basal } IOB_t}$$

and the Total IOB Ratio may be compared to a threshold (e.g., 0.5, meaning the Total IOB is half or less than the IOB that would be present if delivering the BBR of insulin). In some cases, the determination of the block 345 may be a subset of and/or may replace the determination of the block 340. If the total IOB is below the first threshold (e.g., if the constraint is triggered), the method 300 may proceed to the block 350. If the total IOB is not below the first threshold, the method 300 may proceed to the block 360.

At block 350, the delivery actions may be adjusted to deliver insulin at the baseline basal rate. For example, the system may transition out of the feedback delivery mode and into the standard delivery mode. As another example, the system may adjust each of the delivery actions to all be 1× the BBR. In some cases, the adjustment or change in mode may occur for a limited time, for a certain number of insulin delivery actions, etc. In some cases, the adjustment or change in mode may occur until the user requests or otherwise causes the device to transition back into the feedback delivery mode.

At block 355, an alert may be provided to the user. For example, the control device may cause an audible alarm, may provide a visual alarm (e.g., a flashing light or an on-screen prompt), etc. In some cases, the alert may identify whether the constraint triggered is related to not receiving a minimum amount of insulin, or delivering an excessive amount of insulin. After the block 355, the method 300 may proceed to the block 365.

At block 360, a determination may be made whether the delivery actions are delivering insulin above a second threshold. For example, the control device may determine whether the Basal IOB Ratio delivered is above a threshold ratio (e.g., 1.90, 1.85, 1.80, 1.75, or 1.70), whether the delivery actions have included 2× the BBR for longer than a threshold amount of time, whether the total amount of basal insulin delivered has met a certain percentage of the total daily basal dose (e.g., 10% of TDBD, 12% of TDBD, 13% of TDBD, 14% of TDBD, 15% of TDBD, 16% of TDBD, 17% of TDBD, 18% of TDBD), etc. If the delivery actions are delivering insulin above the second threshold (e.g., the constraint regarding excessive insulin delivery has been triggered), the method 300 may proceed to the block 350. If the delivery actions are not delivering insulin above the second threshold, the method 300 may return to the block 305.

At block 365, a determination may be made whether an acknowledgment has been received from the user regarding the alert, the constraint, the modification of the delivery actions, and/or the transitioning to the standard delivery mode. In some cases, the acknowledgment may include a request to transition from the standard delivery mode to the feedback delivery mode.

At block 370, delivery of insulin at the predetermined variations of the baseline basal rate may be permitted. For example, the control device may transition to the feedback delivery mode.

Modifications, additions, or omissions may be made to the method 300 without departing from the scope of the present disclosure. For example, the operations of the method 300 may be implemented in differing order. Additionally or alternatively, two or more operations may be performed at the same time. Furthermore, the outlined operations and actions are provided as examples, and some of the operations and actions may be optional, combined into fewer operations and actions, or expanded into additional operations and actions without detracting from the essence of the disclosed embodiments. For example, in some embodiments, the blocks 320, 325, 330, and 335 may be removed. As another example, in some embodiments, the blocks 355, 365, and 370 may be omitted. As an additional example, in some cases, the blocks 340 and/or 345 may be performed at the same time as the block 360.

Figure 4:
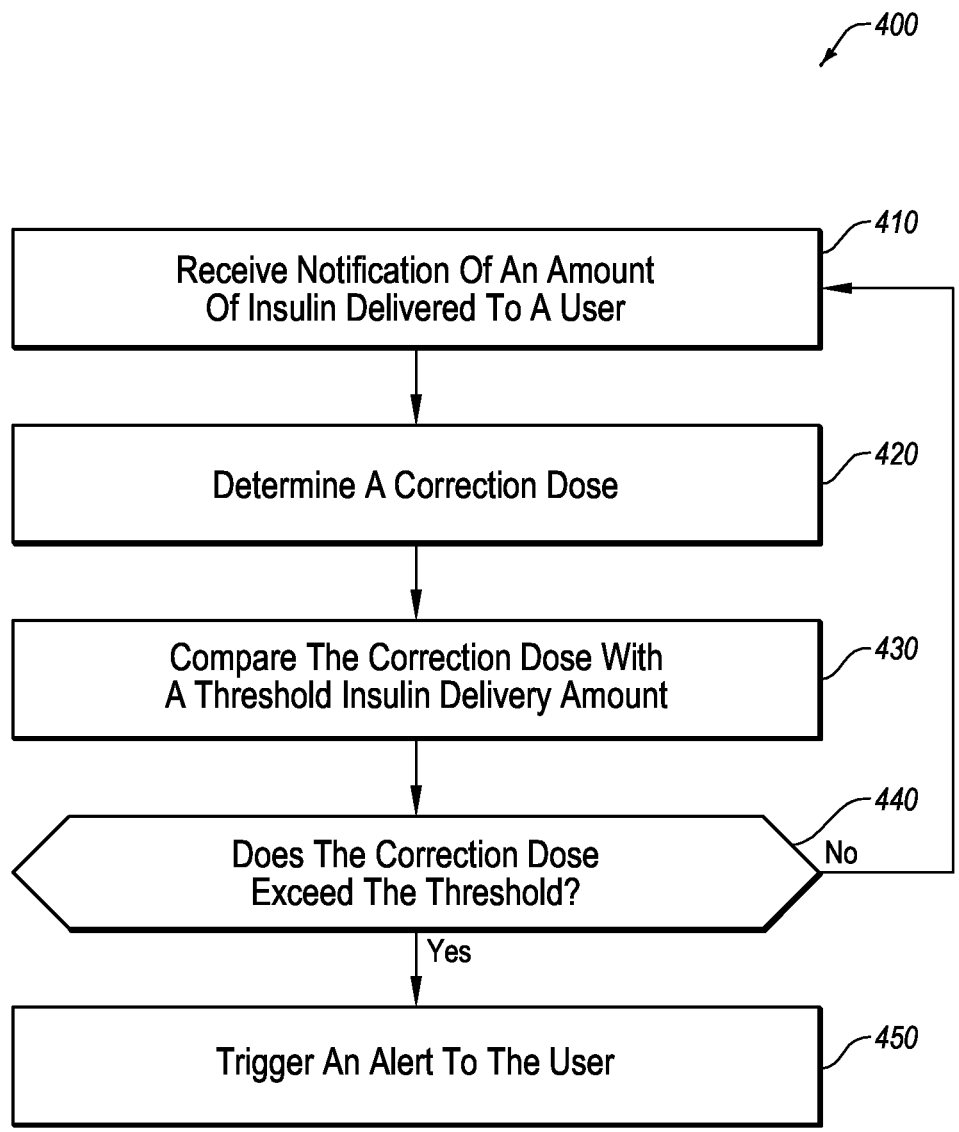
FIG. 4 illustrates a flowchart of an example method of providing an alert associated with a correction dose.

FIG. 4 illustrates a flowchart of an example method 400 of providing an alert associated with a correction dose, in accordance with one or more embodiments of the present disclosure. The method 400 may be performed by any suitable system, apparatus, or device. For example, the system 10, the pump assembly 15, the control device described with reference to FIG. 1, and/or a remote server may perform one or more of the operations associated with the method 400. Although illustrated with discrete blocks, the steps and operations associated with one or more of the blocks of the method 400 may be divided into additional blocks, combined into fewer blocks, or eliminated, depending on the desired implementation.

At block 410, a notification may be received of an amount of insulin delivered to a user. For example, with reference to FIG. 1, the pump assembly 15 may provide a notification to the control device that the user received a dose of insulin. The dose of insulin may be related to a basal amount of insulin, a bolus dose of insulin, or both. In some cases, the notification may be one of many notifications such that the control device may track the delivery of insulin to the user, including delivery of basal insulin, bolus insulin, or both.

At block 420, a correction dose may be determined. For example, the control device may determine a correction bolus to be delivered to the user to address a high blood glucose level. In these and other embodiments, the correction bolus may be determined based on EGV, Target, ISF, and IOB as described above.

At block 430, the correction does may be compared with a threshold insulin delivery amount. In some cases, the threshold insulin delivery amount may include a static amount of insulin (e.g., a set number of units of insulin). In some cases, the threshold insulin delivery amount may include an amount based on a portion of daily basal insulin, such as one hour's worth of the TDBD, or the accumulation of basal insulin based on a personalized rate over a given period of time. In these and other embodiments, the threshold amount may be multiplied by a factor that may affect how readily an alert or alarm may be triggered.

At block 440, a determination may be made whether the correction dose exceeds the threshold. If the correction dose exceeds the threshold, the method 400 may proceed to the block 450. If the correction dose does not exceed the threshold, the method 400 may return to the block 410 where additional notifications of insulin delivery may be received.

At block 450, an alert may be triggered to the user. For example, an audible alert or alarm, a visual alert or alarm, a textual message, etc., may be provided to the user to indicate that the amount of insulin in the correction bolus exceeds the threshold.

Modifications, additions, or omissions may be made to the method 400 without departing from the scope of the present disclosure. For example, the operations of the method 400 may be implemented in differing order. Additionally or alternatively, two or more operations may be performed at the same time. Furthermore, the outlined operations and actions are provided as examples, and some of the operations and actions may be optional, combined into fewer operations and actions, or expanded into additional operations and actions without detracting from the essence of the disclosed embodiments.

Figure 5:
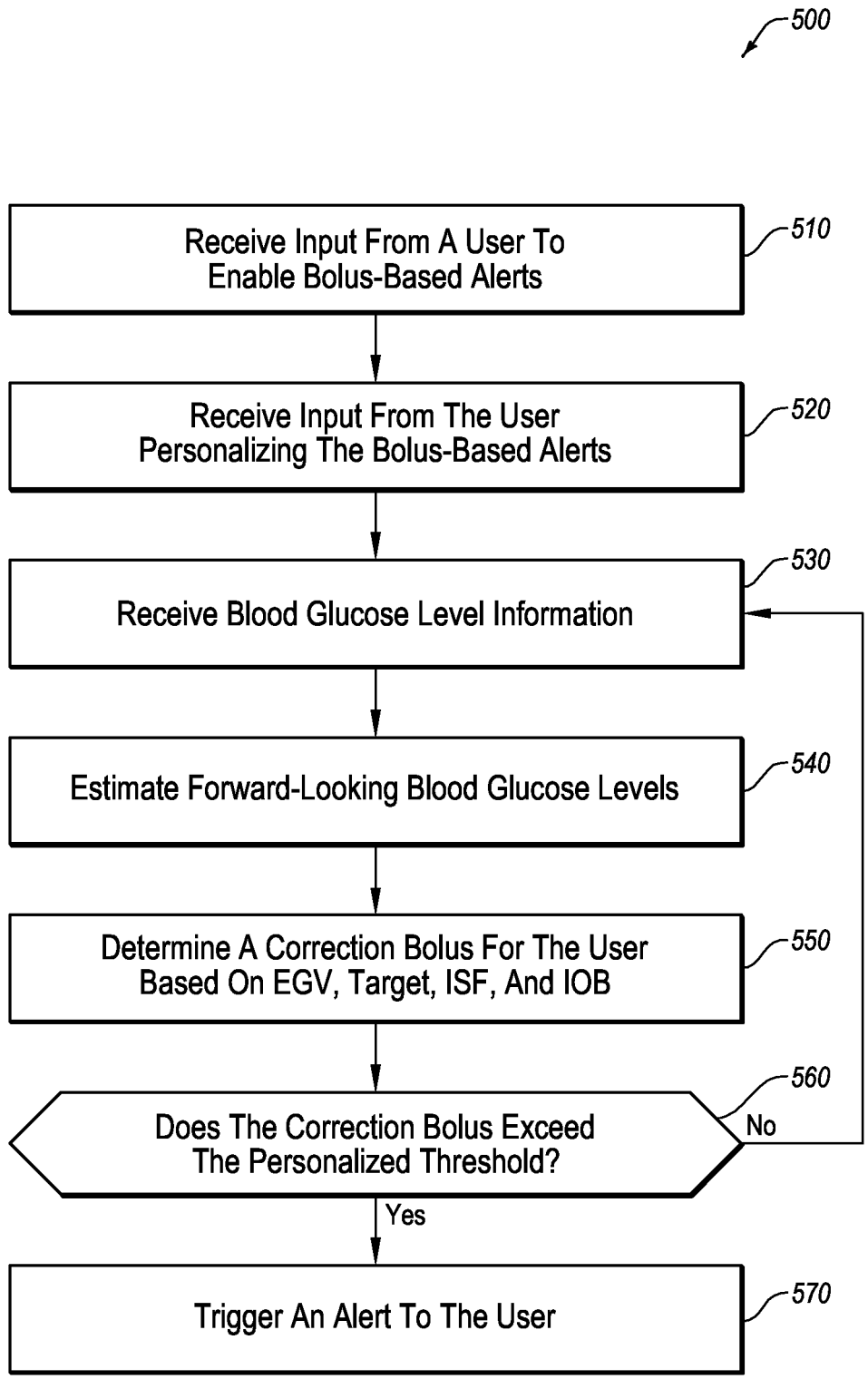
FIG. 5 illustrates a flowchart of an example method of providing an alert associated with a correction bolus.

FIG. 5 illustrates a flowchart of an example method 500 of providing an alert associated with a correction bolus, in accordance with one or more embodiments of the present disclosure. The method 500 may be performed by any suitable system, apparatus, or device. For example, the system 10, the pump assembly 15, the control device described with reference to FIG. 1, and/or a remote server may perform one or more of the operations associated with the method 500. Although illustrated with discrete blocks, the steps and operations associated with one or more of the blocks of the method 500 may be divided into additional blocks, combined into fewer blocks, or eliminated, depending on the desired implementation.

At block 510, an input may be received from a user to enable bolus-based alerts. For example, a user may utilize a display device (such as the display device 60 of FIG. 1) to interact with a control device to indicate that the user desires to receive bolus-based alerts. Such alerts may indicate, for example, when a correction bolus is excessively large as compared to the basal insulin the user is receiving.

At block 520, input from the user to personalize the bolus-based alerts may be received. For example, the user may input a specific bolus amount to act as the threshold. As another example, the user may input a multiplicative factor that may affect how readily an alert or alarm will be triggered (e.g., changing how large the bolus does is compared to the basal insulin before an alert is triggered). In some cases, the user may input a particular value (e.g., 0.5, 0.75, 1, 1.5, 2, 3, etc.). In some cases, the user may be presented with a query and the factor may be selected based on the response of the user. For example, the user may be queried how readily or how sensitive or how responsive they would like the system to be with regards to providing alerts for correction bolus sizes relative to the basal insulin. Based on the response, the system may automatically provide or utilize a factor.

At block 530, blood glucose level information may be received. For example, the control device may receive blood glucose level information from one or more blood glucose monitors of the diabetes management system. In these and other cases, the blood glucose level information may be obtained by swiping a display device, a pump, a bolus administering device, etc., past a flash glucose monitor. Additionally or alternatively, a blood glucose monitoring device may periodically or regularly provide the blood glucose level information to the control device. In some cases, the user may manually input the blood glucose level information. For example, the user may use the display device to input a bolus being delivered to the user.

At block 540, forward-looking blood glucose levels may be estimated. For example, the control device may predict one or more future blood glucose levels based on one or more parameters such as IOB, historical BGV, ISF, CR, etc. In these and other cases, the estimated blood glucose level may be estimated for a time in the future. Additionally or alternatively, the blood glucose level may be estimated based on blood glucose level information obtained from the block 530. In addition to forward-looking blood glucose levels, in some cases, the block 540 may estimate a current blood glucose level.

At block 550, a correction bolus for the user may be determined based on EGV, Target, ISF, and IOB. For example, a correction bolus may be determined according to the equation:

$$\frac{EGV - \text{Target}}{ISF} - IOB$$

In some cases, the block 550 may determine the correction bolus according to any approach or algorithm that attempts to address a high blood glucose level with a bolus of insulin.

At block 560, a determination may be made whether the correction bolus exceeds the personalized threshold. For example, the correction bolus determined at the block 550 may be compared to a threshold amount of insulin multiplied by the factor from the block 520. In some cases, the threshold may be based on a static amount of insulin. In some cases, the threshold may be dynamic and may be based on an amount of insulin for a portion of the TDBD, such as one hour's worth of the TDBD of insulin. In some cases, the threshold may be based on an accumulated amount of insulin based on personalized BBR for one or more diurnal time periods. For example, if a user's BBR is 3 U/hour during one hour and 4 U/hour during the next hour, and the time period being monitored is from half-way through the first hour and the threshold is based on the next one hour, the threshold amount of insulin may be (0.5 hour*3 U/hour)+ (0.5 hour*4 U/hour)=3.5 U and if the user has designated a factor of 2 (meaning the correction bolus must be high before the user is alerted), the threshold amount of insulin may be 7 U. If the correction bolus exceeds the threshold, the method 500 may proceed to the block 570. If the correction bolus does not exceed the threshold, the method 500 may return to the block 530 where additional blood glucose level information may be received.

At block 570, an alert may be triggered to the user indicating that the correction bolus is above the threshold amount of insulin. The block 570 may be similar or comparable to the block 450.

Modifications, additions, or omissions may be made to the method 500 without departing from the scope of the present disclosure. For example, the operations of the method 500 may be implemented in differing order. Additionally or alternatively, two or more operations may be performed at the same time. Furthermore, the outlined operations and actions are provided as examples, and some of the operations and actions may be optional, combined into fewer operations and actions, or expanded into additional operations and actions without detracting from the essence of the disclosed embodiments.

The embodiments described herein may include the use of a special-purpose or general-purpose computer including various computer hardware or software modules, as discussed in greater detail below.

Embodiments described herein may be implemented using computer-readable media for carrying or having computer-executable instructions or data structures stored thereon. Such computer-readable media may be any available media that may be accessed by a general-purpose or special-purpose computer. By way of example, and not limitation, such computer-readable media may include non-transitory computer-readable storage media including Random-Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage medium which may be used to carry or store desired program code in the form of computer-executable instructions or data structures and which may be accessed by a general-purpose or special-purpose computer. Combinations of the above may also be included within the scope of computer-readable media.

Computer-executable instructions comprise, for example, instructions and data, which cause a general-purpose computer, special-purpose computer, or special-purpose processing device (e.g., one or more processors) to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the terms "module" or "component" may refer to specific hardware implementations configured to perform the operations of the module or component and/or software objects or software routines that may be stored on and/or executed by general-purpose hardware (e.g., computer-readable media, processing devices, etc.) of the computing system. In some embodiments, the different components, modules, engines, and services described herein may be implemented as objects or processes that execute on the computing system (e.g., as separate threads). While some of the system and methods described herein are generally described as being implemented in software (stored on and/or executed by general-purpose hardware), specific hardware implementations or a combination of software and specific hardware implementations are also possible and contemplated. In the present description, a "computing entity" may be any computing system as previously defined herein, or any module or combination of modulates running on a computing system.

Any ranges expressed herein (including in the claims) are considered to be given their broadest possible interpretation. For example, unless explicitly mentioned otherwise, ranges are to include their end points (e.g., a range of "between X and Y" would include X and Y). Additionally, ranges described using the terms "substantially," "approximately," or "about" are to be understood to be given their broadest meaning consistent with the understanding of those skilled in the art. Additionally, the term approximately includes anything within 10%, 5%, or 1%, or within manufacturing or typical tolerances.

While certain embodiments have been described and shown in the accompanying drawings, such embodiments are merely illustrative and not restrictive of the scope of the disclosure, and this disclosure is not limited to the specific constructions and arrangements shown and described, since various other additions and modifications to, and deletions from, the described embodiments will be apparent to one of ordinary skill in the art. Thus, the scope of the disclosure is only limited by the literal language, and legal equivalents, of the claims that follow.

What is claimed is:

1. A method of insulin delivery, the method comprising:
   based on blood glucose readings of a user, generating a set of insulin delivery actions including delivery of a baseline basal rate;
   monitoring insulin delivery actions delivering predefined variations of the baseline basal rate that are above the baseline basal rate to determine whether previous insulin delivery actions have delivered insulin beyond a threshold amount; and
   responsive to insulin being delivered beyond the threshold amount, adjusting the set of insulin delivery actions.

2. The method of claim 1, wherein the threshold amount includes at least a portion of a total daily basal dose.

3. The method of claim 1, wherein adjusting the set of insulin delivery actions includes changing only a portion of the delivery actions of the set of delivery actions.

4. The method of claim 1, wherein adjusting the set of insulin delivery actions includes changing all delivery actions in the set of delivery actions to deliver insulin according to the baseline basal rate.

5. The method of claim 1, wherein determining whether previous insulin delivery actions have delivered insulin beyond a threshold amount is determined by:

$$\text{Total } IOB \text{ Ratio} = \frac{\text{Nominal Basal } IOB_t + \text{Bolus } IOB_t + \text{Basal Adjust } IOB_t}{\text{Nominal Basal } IOB_t}$$

6. The method of claim 1, further comprising including approximately 0.17 of a total daily basal dose in the threshold amount.

7. The method of claim 1, wherein the threshold amount comprises an amount of insulin delivered via a plurality of consecutive insulin delivery actions above the baseline basal rate for a threshold amount of time.

8. The method of claim 7, wherein the threshold amount of time comprises one of approximately two hours, three hours, four hours, five hours, or six hours.

9. The method of claim 1, wherein the predefined variations of the baseline basal rate include at least one of 0×, 1×, 2×, or 3× the baseline basal rate.

10. The method of claim 1, further comprising:
    receiving an acknowledgement of the adjustment to the set of insulin delivery actions; and
    in response to receiving the acknowledgment, allowing insulin to be delivered according to the adjusted set of insulin delivery actions.

11. The method of claim 1, further comprising:
    receiving an indication that the user is transitioning from a first type of insulin delivery to a second type of insulin delivery; and
    in response to receiving the indication, adjusting the threshold amount such that insulin delivery below the baseline basal rate is allowed until a predefined period of time after a delivery of insulin according to the first type of insulin delivery.

12. The method of claim 1, further comprising:
    receiving an indication that the user is transitioning from a first type of insulin delivery to a second type of insulin delivery; and
    in response to receiving the indication, reducing the baseline basal rate for a predefined period of time after a delivery of insulin according to the first type of insulin delivery.

13. The method of claim 12, wherein reducing the baseline basal rate comprises reducing the baseline basal rate to approximately 25% of the baseline basal rate.

14. A method of insulin delivery, the method comprising:
    based on blood glucose readings of a user, generating a set of insulin delivery actions including delivery of a baseline basal rate;
    calculating an amount of basal insulin on board (JOB) due to execution of one or more the insulin delivery actions; and
    delivering insulin at or below the baseline basal rate whenever basal IOB exceeds a threshold amount.

15. The method of claim 14, further comprising determining the threshold amount by calculating a basal IOB Ratio comparing the basal IOB to an insulin on board assuming only the baseline basal rate has been delivered.

16. The method of claim 15, wherein the basal IOB Ratio within a range of about 1.6 to about 1.9.

17. The method of claim 14, further comprising determining the threshold amount by calculating an amount of insulin on board that exceeds a defined percentage an average daily dosage of basal insulin for the user.

18. The method of claim 17, wherein defined the percentage is within a range of about 10% to about 25% of the average daily dosage of basal insulin for the user.

19. An insulin delivery monitoring system comprising:
   an insulin delivery device configured to deliver insulin to a user; and
   a controller comprising:
      at least one processor; and
      at least one non-transitory computer-readable storage medium storing instructions thereon that, when executed by the at least one processor, cause the controller to:
         based on blood glucose readings of a user, generate a set of insulin delivery actions including delivery of a baseline basal rate;
         monitoring insulin delivery actions delivering predefined variations of the baseline basal rate that are above the baseline basal rate; and
         based on the previous insulin delivery actions, adjusting the set of insulin delivery actions.

20. The insulin delivery monitoring system of claim 19, further comprising instruction that, when executed by the at least one processor, cause the controller to: determine whether previous insulin delivery action have delivered insulin beyond a threshold amount.

* * * * *

UNITED STATES PATENT AND TRADEMARK OFFICE
CERTIFICATE OF CORRECTION

| | | |
|---|---|---|
| PATENT NO. | : 11,969,579 B2 | |
| APPLICATION NO. | : 17/303974 | |
| DATED | : April 30, 2024 | |
| INVENTOR(S) | : Bryan Mazlish and Lane Desborough | |

It is certified that error appears in the above-identified patent and that said Letters Patent is hereby corrected as shown below:

In the Claims

Claim 14, Column 28, Line 55, change "on board (JOB) due" to --on board (IOB) due--

Signed and Sealed this
Thirteenth Day of August, 2024

Katherine Kelly Vidal
*Director of the United States Patent and Trademark Office*